United States Patent
Stowell et al.

(12)

(10) Patent No.: US 6,388,080 B1
(45) Date of Patent: May 14, 2002

(54) POLYMORPHIC FORMS OF 6-[4-(1-CYCLOHEXYL-1H-TETRAZOL-5-YL) BUTOXY]-3,4-DIHYDRO-2(1H)-QUINOLINONE

(76) Inventors: Grayson Walker Stowell, 710 Darwin Dr., Wilmington, NC (US) 28405; Robert R. Whittle, 5006 Pine Needles Dr., Wilmington, NC (US) 28403

(*) Notice: Subject to any disclaimer, the term of this patent is extended or adjusted under 35 U.S.C. 154(b) by 0 days.

(21) Appl. No.: 09/896,448

(22) Filed: Jun. 29, 2001

(51) Int. Cl.[7] ............................................. C07D 401/12
(52) U.S. Cl. ......................................................... 546/155
(58) Field of Search .......................................... 546/155

(56) References Cited

U.S. PATENT DOCUMENTS

| | | |
|---|---|---|
| 4,277,479 A | 7/1981 | Nishi et al. |
| 4,728,653 A | 3/1988 | Campbell et al. |
| 4,740,513 A | 4/1988 | Campbell et al. |
| 4,803,162 A | 2/1989 | Smith et al. |
| 4,837,334 A | 6/1989 | Campbell et al. |
| 4,900,839 A | 2/1990 | Campbell et al. |
| 5,008,274 A | 4/1991 | Nishi et al. |
| 5,017,583 A | 5/1991 | Young et al. |
| 5,064,837 A | 11/1991 | McCombie |
| 5,079,264 A | 1/1992 | MaClean et al. |
| 5,318,971 A | 6/1994 | McCombie |
| 5,401,754 A | 3/1995 | Fujioka et al. |
| 5,434,164 A | 7/1995 | Nishi et al. |
| 5,506,239 A | 4/1996 | Sato et al. |
| 5,512,575 A | 4/1996 | Jacobs et al. |
| 5,532,253 A | 7/1996 | Fujioka et al. |
| 5,658,926 A | 8/1997 | Sato et al. |
| 5,763,454 A | 6/1998 | Handanyan et al. |
| 5,985,893 A | 11/1999 | Yu et al. |
| 6,001,856 A | 12/1999 | Dow |
| 6,080,757 A | 6/2000 | Brown |

OTHER PUBLICATIONS

Nishi et al., "Studies on 2–Oxoquinoline as Blood Platelet Aggregation Inhibitors. II. 6–[3–(1–Cyclohexyl–5–tetrazoly[1])propoxy]–1,2–dihydro–2–oxoquinoline and Related Compounds," Chem. Pharm. Bull. 21(4), 1151–1157 (1983).

*Primary Examiner*—Patricia L. Morris
(74) *Attorney, Agent, or Firm*—Myers Bigel Sibley & Sajovec, P.A.; Steven A. Fontana, Esq.

(57) ABSTRACT

Polymorphs Form B, Form C, and amorphous of 6-[4-(1-cyclohexyl-1H-tetrazol-5-yl)butoxy]-3,4-dihydro-2(1H)-quinolinone, commonly known as cilostazol, have been identified. These polymorphs may be formed in pure form, in combination with each other, in combination with other polymorphs of cilostazol, or together with other pharmaceutical agents. Processes for preparing these polymorphs, and combinations of these polymorphs, as well as methods of use and unit dosages of these polymorphic forms, and their combinations, are described.

14 Claims, 25 Drawing Sheets

POLYMORPHIC FORMS OF 6-[4-(1-CYCLOHEXYL-1H-TETRAZOL-5-YL)BUTOXY]-3,4-DIHYDRO-2(1H)-QUINOLINONE

BACKGROUND OF THE INVENTION

1. Field of the Invention

The present invention relates to compositions and methods of preparing novel forms of the free base of 6-[4-(1-cyclohexyl-1H-tetrazol-5-yl)butoxy]-3,4-dihydro-2(1H)-quinolinone (hereinafter referred to by its generice name "cilostazol"). More particularly, novel crystalline forms of cilostazol, in the form of polymorphs B, C, and amorphous are disclosed. Most particularly, such forms of cilostazol, individually and in combinations thereof, with and without polymorphic Form A, are useful in pharmaceutical formulations and methods for using such polymorphs and formulations therof.

2. Description of Related Art

The compound 6-[4-(1-cyclohexyl-1H-tetrazol-5-yl)butoxy]-3,4-dihydro-2(1H)-quinolinone is generally known as the pharmaceutically active compound cilostazol. Cilostazol has been known to have a singular crystalline form (Form A), which is a free base and used as an active pharmaceutical ingredient (API) for use in the preparation of drug products Cilostazol has the following chemical structure:

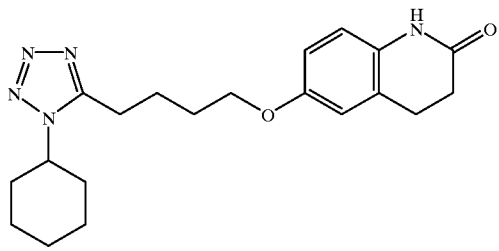

Cilostazol, and several of its metabolites, are known inhibitors of phosphodiesterase and, more particularly, phosphodiesterase III. As a phosphodiesterase inhibitor (type III), cilostazol suppresses platelet aggregation and also acts as a direct arterial vasodilator. In addition to its reported vasodilator and antiplatelet effects, cilostazol has been proposed to have beneficial effects on plasma lipoproteins, increasing plasma high density lipoprotein cholesterol and apolipoprotein (See e.g., Dawson et al., Circulation 98: 678–686 [1998]; Elam et al., Arterioscler Thromb. Vasc. Biol. 18: 1942–1947[1998]; Drug Evaluation Monographs, vol. 99, Micromedex Inc.). Additionally, cilostazol has been reported as useful for the treatment of sexual dysfunction in U.S. Pat. No. 6,187,790 to Cutler. Cilostazol free base is the API in the pharmaceutical drug product marketed under the trademark PLETAL® (Otsuka America Pharmaceutical, Inc., Rockville, Md.; and Pharmacia Company, Kalamazoo, Mich.).

Methods of preparation of cilostazol are set forth by Nishi et al. (Chem. Pharm. Bull. 31: 1151[1983], and U.S. Pat. No. 4,277,479, the disclosure of both references are hereby incorporated by reference, and its pharmacology, metabolism, mechanism of action and clinical evaluations are described in Arzneimittel–Forsch. 35: 1117-1208(1985).

Use of cilostazol in pharmaceutical formulations has been limited by its low aqueous solubility and low bioavailability, which impede its efficient therapeutic use. Therefore, it would be beneficial if pharmaceutical chemists could provide a more soluble and, thus, more bioavailable drug product. These forms could lead to lower doses of drug substance (per unit dose and per day) required to be administered to provide similar efficacy and, potentially, a better safety profile, to patients in need of treatment. To date, no such forms have been prepared.

Polymorphic forms of the same drug substance or API, as administered by itself or formulated as a drug product (also known as the final or finished dosage form), are well known in the pharmaceutical art to affect, for example, the solubility, stability, flowability, tractability, and compressibility of drug substances and the safety and efficacy of drug products (see, e.g., Knapman, K. *Modern Drug Discoveries,* March, 2000: 53). So critical are the potential effects of different polymorphic forms in a single drug substance on the safety and efficacy of the respective drug products(s) that the United States Food and Drug Administration (FDA) requires each drug substance manufacturer, at least, to control its synthetic processes such that the percentages of the various respective polymorphic forms, when present, must be controlled and consistent among batches and within the drug substance/product's specification as approved by the FDA.

SUMMARY OF THE INVENTION

Form A is the material produced using the methods described in U.S. Pat. No. 4,277,479 (hereinafter referred to as "the '479 patent") and is clearly distinguishable from other polymorphic forms of the present invention by X-ray powder diffraction and other methods of solid state characterization. Form A, the sole, previously known form of cilostazol, as prepared by the procedures described in the '479 patent, has been found to have low aqueous solubility and low-bioavailability. As such, Form A is not particularly well suited for commercial use in pharmaceutical formulations or for therapeutic use.

A novel crystalline form of cilostazol, Form B, which possesses distinct advantages over the previously known Form A of cilostazol has now been prepared and characterized. In accordance with the present invention, a newly discovered polymorph, Form B of cilostazol, can be obtained in a pure form or in combination with other polymorphic forms of cilostazol. Form B is stable, and can be prepared free from contamination by solvates such as water or organic solvents such as, for example, acetonitrile. As such, Form B is useful for the commercial preparation of pharmaceutical formulations such as tablets and capsules.

Another novel crystalline form of cilostazol, Form C, that has also been prepared and characterized, possesses distinct advantages over the previously known Form A of cilostazol, and is clearly distinguishable from other polymorphic forms of the present invention by X-ray powder diffraction and other methods of solid-state characterization. In accordance with the present invention, Form C of cilostazol, can be obtained in a pure form or in combination with other polymorphic forms of cilostazol. Form C is stable, and can be prepared free from contamination by solvates such as water or organic solvents such as, for example, acetonitrile. As such, Form C is also useful for the commercial preparation of pharmaceutical formulations such as tablets and capsules.

Another polymorphic form, amorphous cilostazol, has also been prepared and characterized. Such amorphous is clearly distinguishable from Form A and other polymorphic forms of cilostazol by X-ray powder diffraction and other solid-state methods of characterization. In accordance with the present invention, the newly discovered amorphous cilostazol can be obtained in a pure form or in combination with other polymorphic forms of cilostazol. Amorphous cilostazol can also be prepared free from other polymorphic forms of cilostazol and contamination by solvates such as water or organic solvents such as, for example, acetonitrile. As such, amorphous cilostazol may be used for commercial pharmaceutical formulations such as tablets and capsules, but is preferably used as an intermediate for the preparation of other polymorphic forms of cilostazol.

Accordingly, it is an object of the present invention to provide novel compositions pharmaceutical formulations, and methods of using the novel polymorphic forms of the present invention, and combinations thereof.

The present invention provides novel pure and combinations of polymorphic forms of cilostazol, each of which are useful for providing more desirable solubility and improved bioavailability characteristics, particularly when administered in pharmaceutical dosage forms.

DETAILED DESCRIPTION OF THE INVENTION

Preparation of Form A cilostazol, 6-[4-(1-cyclohexyl-1H-tetrazol-5-yl)butoxy]-3,4-dihydro-2(1H)-quinolinone, is described in U.S. Pat. No. 4,277,479, the disclosure of such patent is herein incorporated by reference. The present invention is directed to polymorphic Form B of cilostazol, Form C of cilostazol, amorphous cilostazol, and combinations thereof, the preparation thereof, pharmaceutical formulations thereof, and the use of such polymorphs, preferably in pharmaceutical formulations, for the therapeutic treatment of subjects in need of treatment. The polymorphic forms of the present invention were characterized using differential scanning calorimetry (DSC), X-ray powder diffraction (XRD), Fourier Transform Infrared Spectroscopy (FTIR), and Fourier Transform Raman Spectroscopy (FT-Raman) analysis as discussed below. Characterization with any of these methods reveals distinctive peaks for each particularly polymorphic form, whether in a pure state or not. For example, pure Form B provides a distinct range of significant peaks when analyzed by XRD. These significant peaks will be present with XRD analysis for pure Form B as well as for samples containing Form B in combination with other polymorphic forms of cilostazol.

Figure 1:
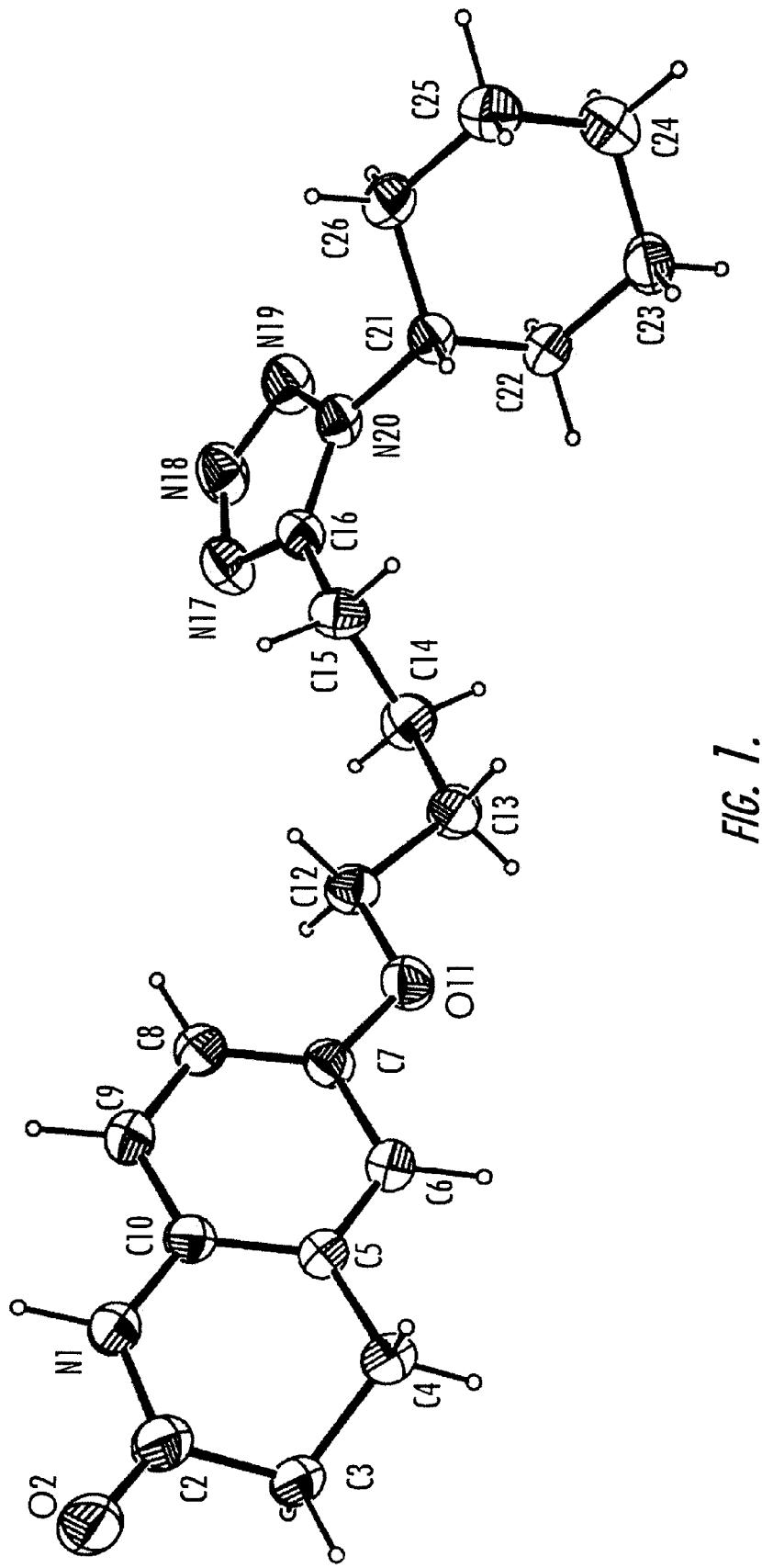
FIG. 1 shows an ORTEP drawing of the single crystal structure of Form A cilostazol.
Figure 2:
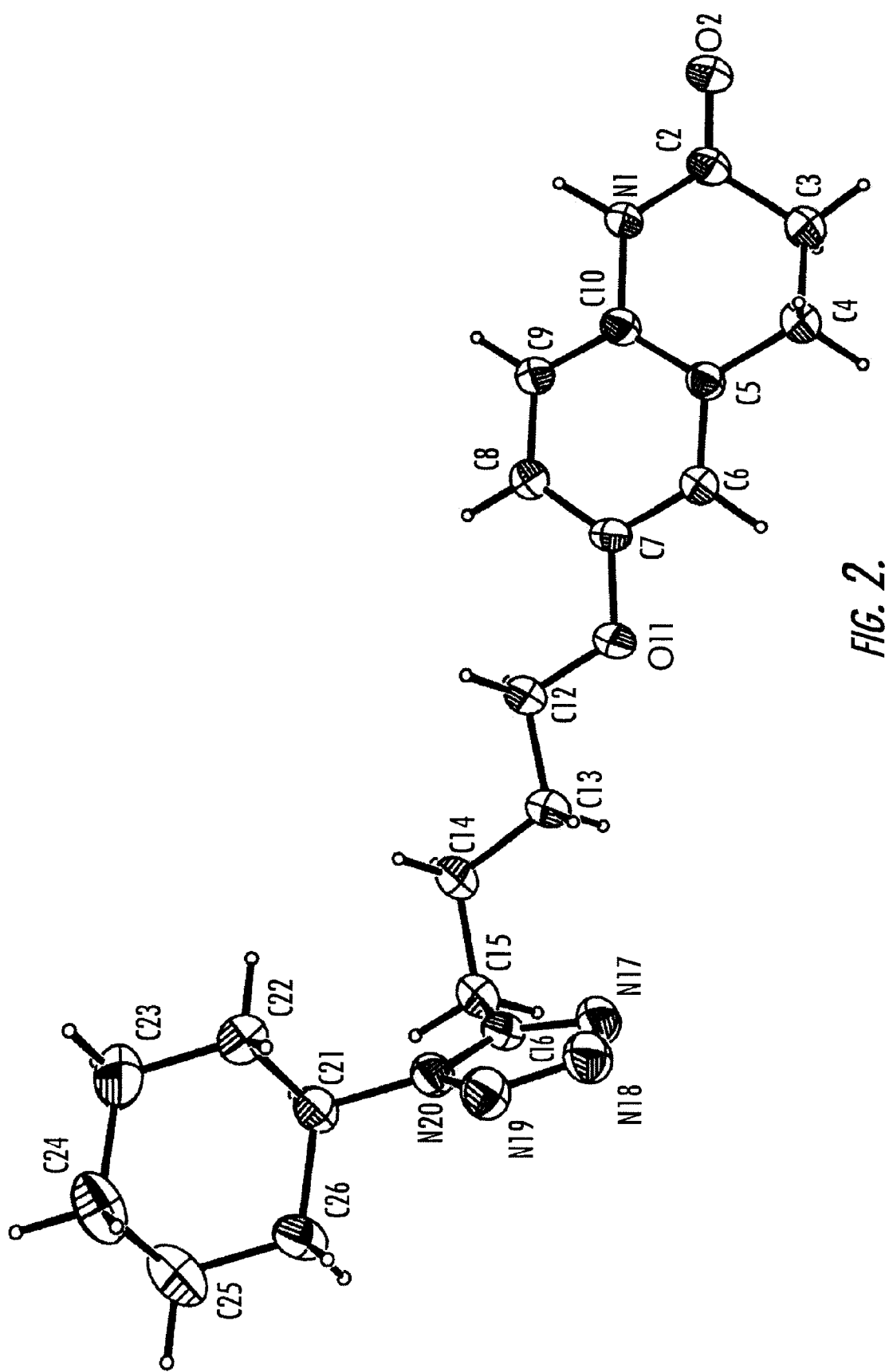
FIG. 2 shows an ORTEP drawing of the single crystal structure of Form C cilostazol.

As seen in FIGS. 1 and 2, as ORTEP drawings of the single crystal structures of Form A of cilostazol and Form C of cilostazol, respectively, show the different orientations of the two cilostazol molecules, thereby distinguishing these two forms of cilostazol. The ORTEP drawings are generated from the Oak Ridge Thermal Ellipsoid Program developed by Oak Ridge National Laboratory in Oak Ridge, Tenn. X-ray single crystal structural analysis was not performed on Form B because of the microcrystalline nature of these samples, or amorphous cilostazol because of the non-crystalline nature thereof.

X-ray single crystal unit cell parameters for Form A of cilostazol and Form C of cilostazol are compared in Table 1, below:

TABLE 1

X-Ray Single Crystal Unit Cell Parameters for Form A and Form C

|  | Form A | Form C |
| --- | --- | --- |
| Crystal Lattice | Orthorhombic | Monoclinic |
| Space Group | Pbca | P2$_1$/n |
| a | 11.3245(4) Å | 5.1476(1) Å |
| b | 9.8527(2) Å | 10.7391(2) Å |
| c | 35.0093(12) Å | 35.2786(7) Å |
| α | 90° | 90° |
| β | 90° | 94.070(1)° |
| γ | 90° | 90° |
| V(Å$^3$) | 3906.2(4) Å$^3$ | 1945.3(1) Å |
| Z | 8 | 4 |

Figure 3:
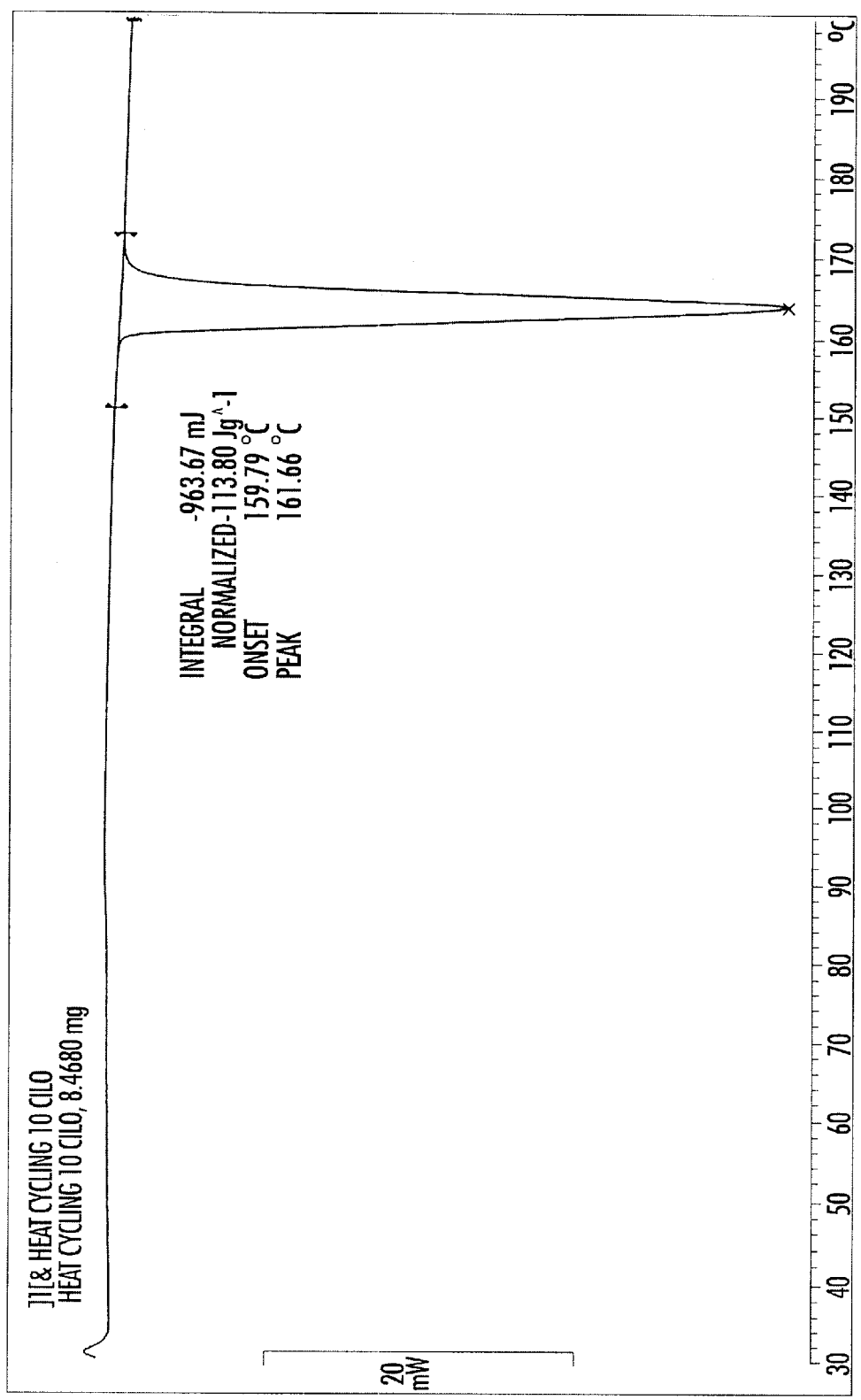
FIG. 3 illustrates a Differential Scanning Calorimetry (DSC) thermogram for Form A cilostazol.
Figure 4:
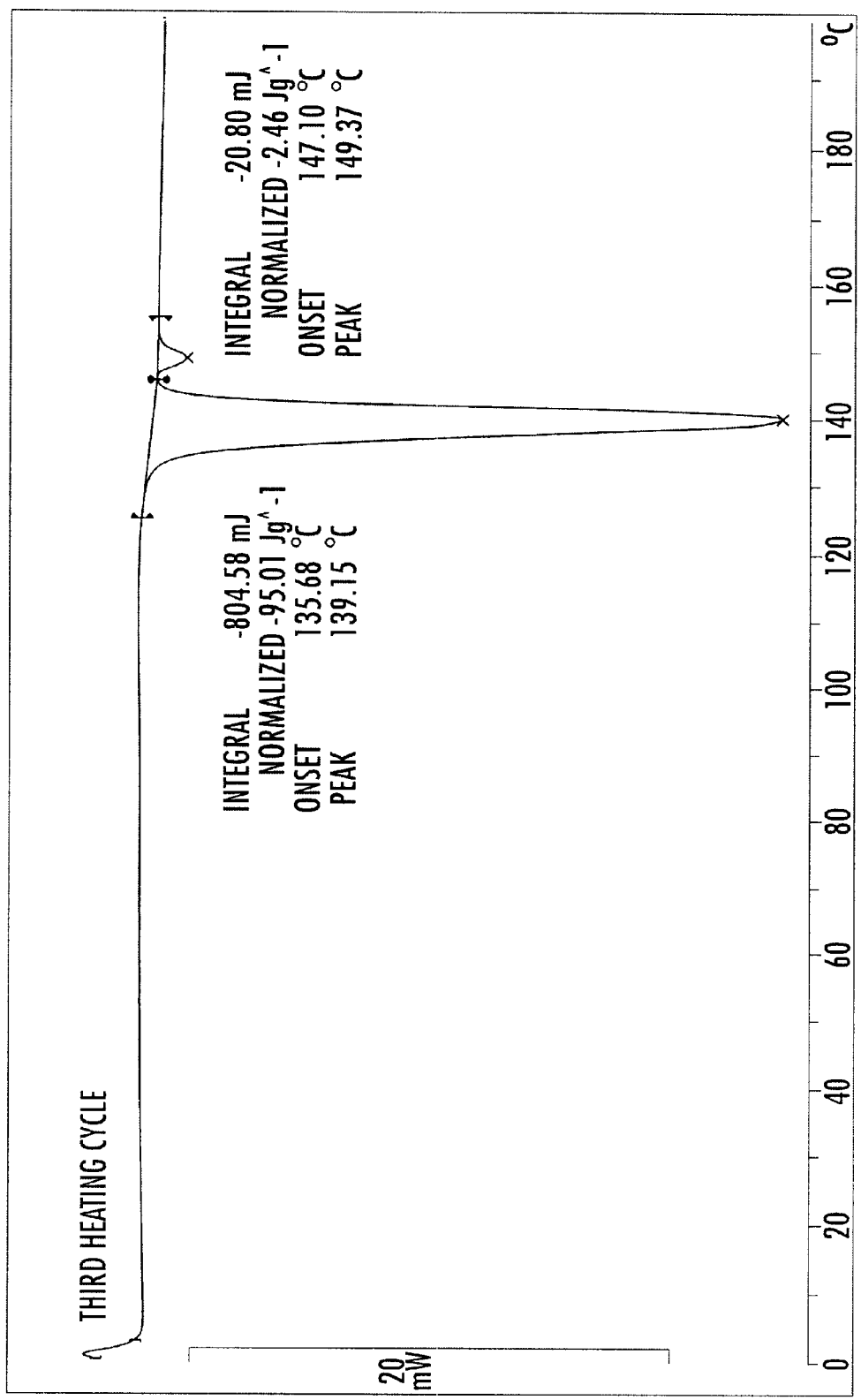
FIG. 4 illustrates a DSC thermogram for Form B cilostazol.
Figure 5:
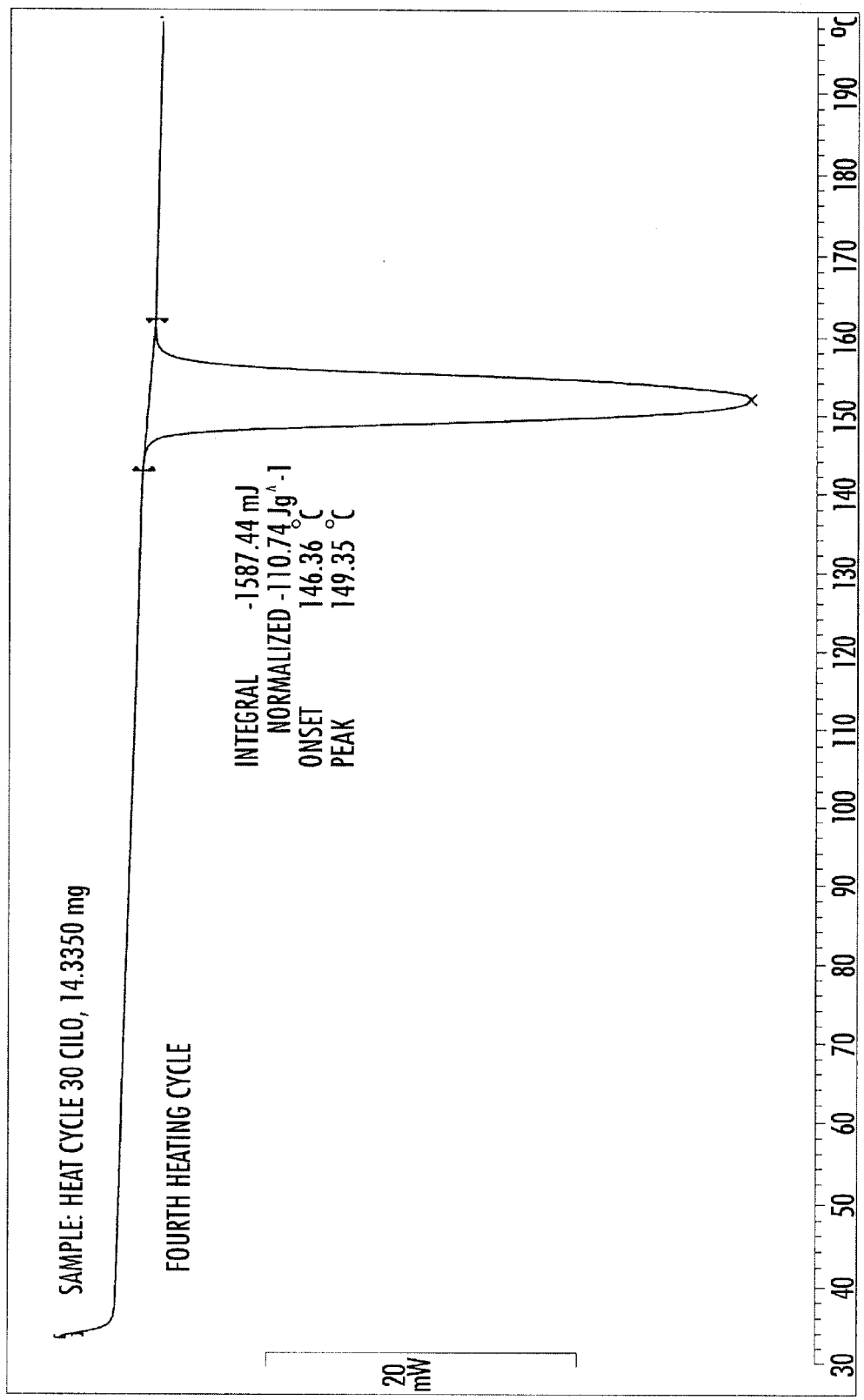
FIG. 5 illustrates a DSC thermogram for Form C cilostazol.
Figure 6:
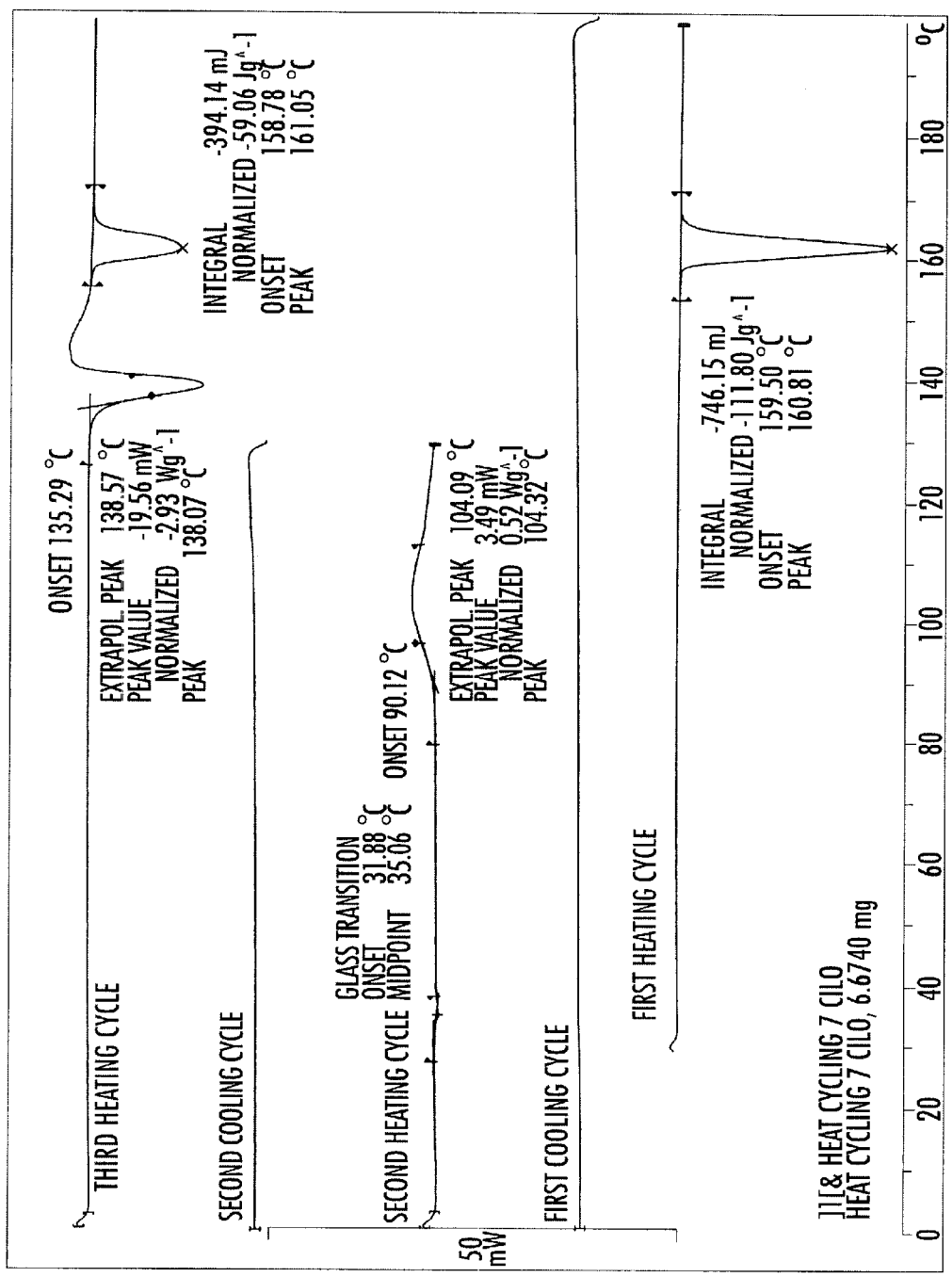
FIG. 6 illustrates a DSC thermogram for the combination of Forms A and B cilostazol.
Figure 7:
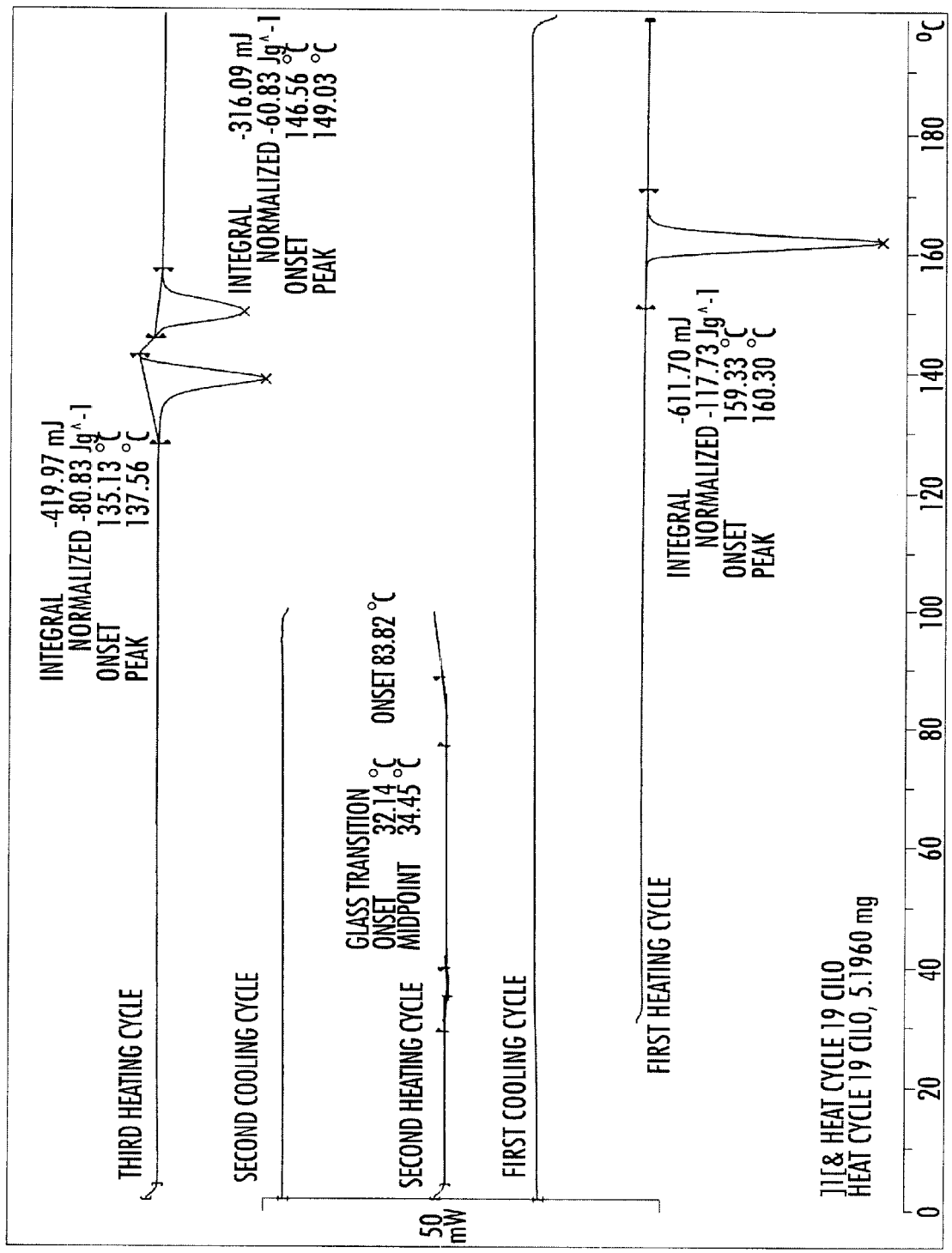
FIG. 7 illustrates a DSC thermogram for the combination of Forms B and C cilostazol.
Figure 8:
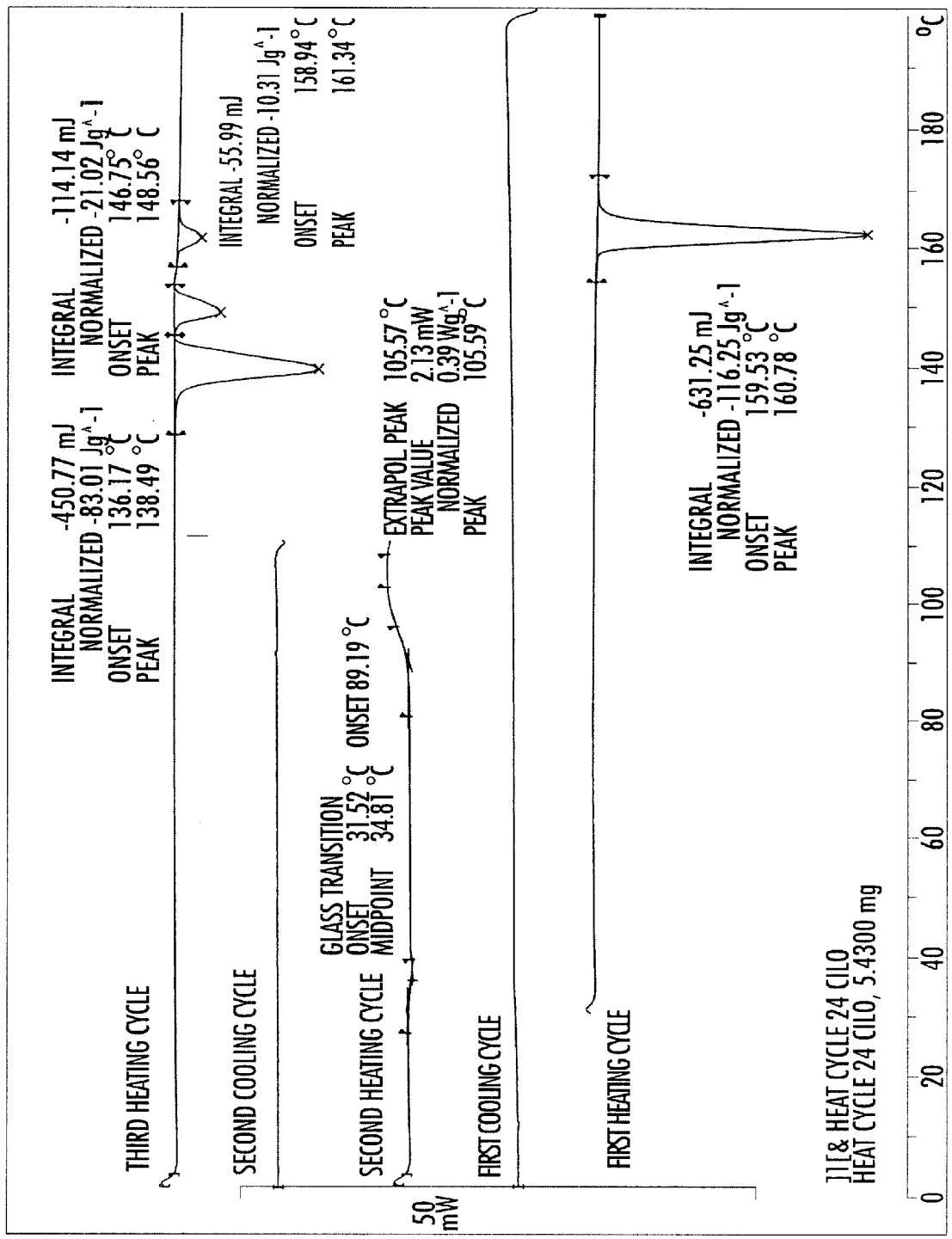
FIG. 8 illustrates a DSC thermogram for the combination of Forms A, B and C cilostazol.

Characterization of Form A of cilostazol, Form B of cilostazol, and Form C of cilostazol was further completed using DSC thermograms, shown in FIGS. 3, 4, and 5, respectively, with DSC thermograms for combinations of Form A and Form B; Form B and Form C; and Forms A, B, and C are shown in FIGS. 6, 7, and 8 respectively. DSC data were generated using a Mettler-Toledo DSC 821$^e$ (Columbus, Ohio) with a Julabo FT900 intercooler chiller (Julabo Company; Allentown, Pa.). In general, samples were analyzed in a vented, sealed aluminum pan. Because the endothermic peak may vary depending upon the rate of heating and the calibration and precision of the instrument, with the amount of peak variation dependent upon the heating rate used, all thermograms included herein were run under the same, consistent conditions: heating at 10° C. per minute under a nitrogen purge at 40 mL/minute.

As seen in FIG. 3, the DSC thermogram for Form A gives an endothermic peak at about 162° C. (onset at about 160° C.). The DSC thermogram shown in FIG. 4 shows an endothermic peak for Form B at about 139° C. (onset at approximately 136° C.). In FIG. 5, the DSC thermogram for Form C also shows an endothermic peak at about 149° C. (onset at about 146° C.).

The DSC thermogram in FIG. 6 shows several heat cycles of a cilostazol sample, with both Form A and Form B of cilostazol present in the third heat cycle. At the bottom of the thermogram, Form A of cilostazol appears during the first heating cycle at about 162° C. Typically, the maximum temperature used for the first heating cycle was from about 180° C. to about 200° C. and, more typically about 200° C. In this instance, after reaching a temperature of about 200° C., the cilostazol was then cooled to about 0° C., which is shown in the first cooling cycle of the DSC thermogram (immediately above the first heating cycle). Once the cilostazol sample reached approximately 0° C., it was immediately reheated to about 130° C., shown in the second heating cycle of the DSC thermogram. During this reheating of the cilostazol sample, the sample appears to pass through a glass transition at about 35° C. (onset at about 32° C), with an exotherm occurring at about 104° C. (onset at about 90° C.). After this reheating, the sample was placed through a second cooling cycle (recooling) to about 0° C., and again reheated in a third heating cycle shown at the top of the DSC thermogram. During the third heating cycle, both Form B and Form A appear, with Form B appearing at about 138° C. (onset at about 135° C.) during this third heating cycle, and Form A appearing at approximately 161° C. (onset at about 159° C.).

FIG. 7 shows a DSC thermogram for the combination of Forms B and Form C in the third heating cycle. The DSC thermogram in FIG. 7 shows several heat cycles using Form A as the starting material. After reaching a temperature of about 200° C. in the first heating cycle, the sample was then cooled to about 0° C. Once the cilostazol sample reached about 0° C., it was immediately reheated to about 100° C, and held at this temperature for about 5 minutes. During this reheating, the cilostazol sample passed through the glass transition temperature at about 35° C. (onset at about 32° C.), but was not permitted to completely proceed through the exotherm which typically starts at about 84° C. by beginning the recooling stage once the temperature reached about 100° C and held for about 5 minutes. This step is critical for the formation of at least some Form C, which is necessary for preparing pure Formn C as taught herein below. After this reheating the sample was placed through a second cooling cycle to approximately 0° C., and again reheated in a third heating cycle as shown at the top of the DSC thermogram. During the third heating cycle, both Form B and Form C are melted, with Form B melting at about 138° C. (onset at about 135° C.), and Form C melting at about 149° C. (onset at about 147° C.). The peaks show a Formn B to Form C peak area ratio of approximately 4:3, respectively, with the relative amount of Form B and Form C further variable on the heat of enthalpy of each polymorphic form.

FIG. 8 illustrates a DSC thermogram for the combination of Form A, Form B and Form C having a second heating cycle with a maximum temperature of about 110° C. with a holding time of about 30 minutes. The peaks in the third heating cycle show a Form A to Form B to Form C peak area ratio of approximately 8:2:1, respectively, with the relative amount of Formn A, Form B and Form C further variable on the heat of enthalpy of each polymorphic form. This thermogram shows Form B and Form C having a lower melting point than Form A, indicating that the crystal packing forces for Forms B and C are not as great as Form A these data strongly suggest that Form B and Form C are more soluble than Form A of cilostazol.

Figure 9:
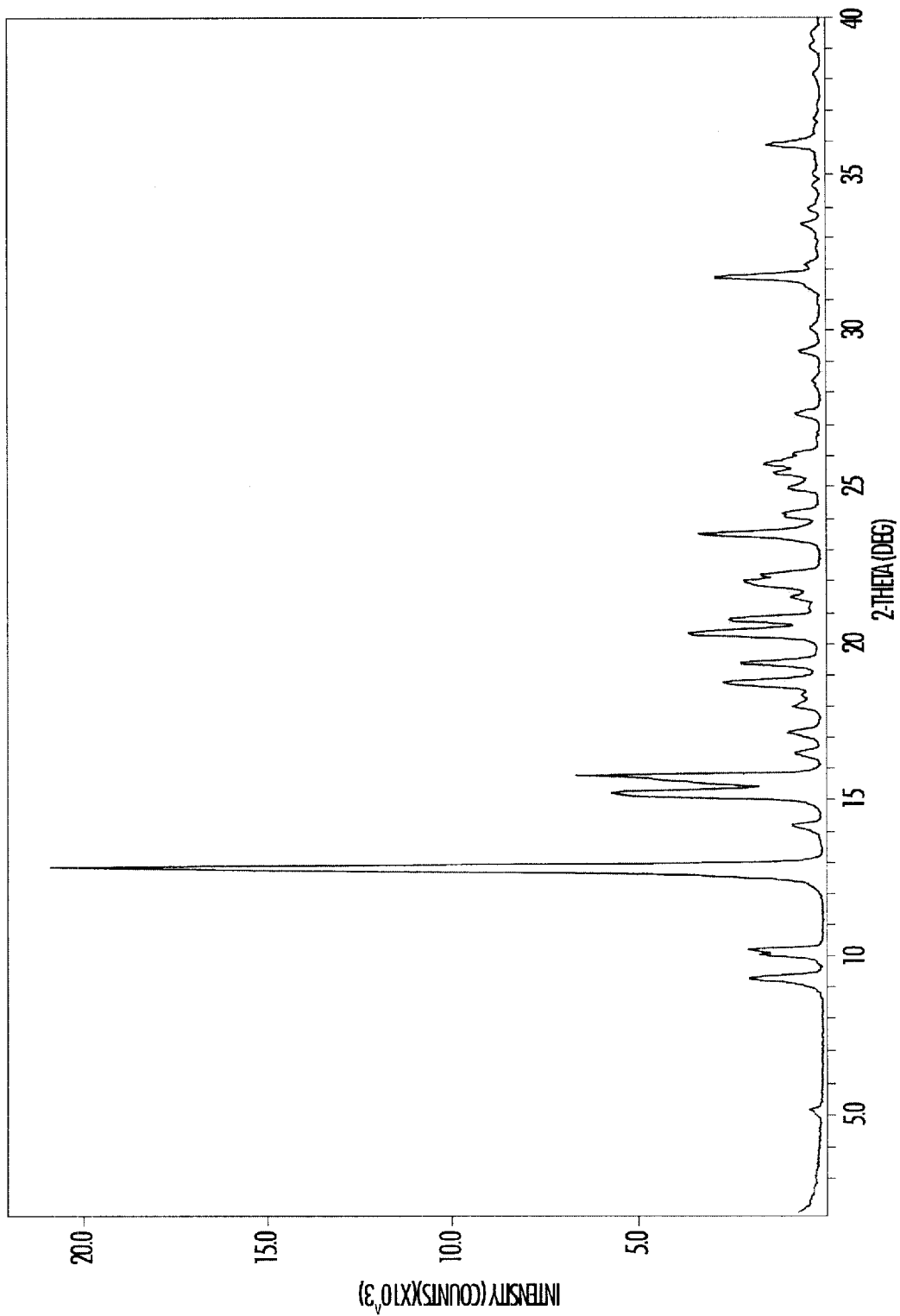
FIG. 9 illustrates an X-ray powder diffraction (XRD) pattern for Form A cilostazol.
Figure 10:
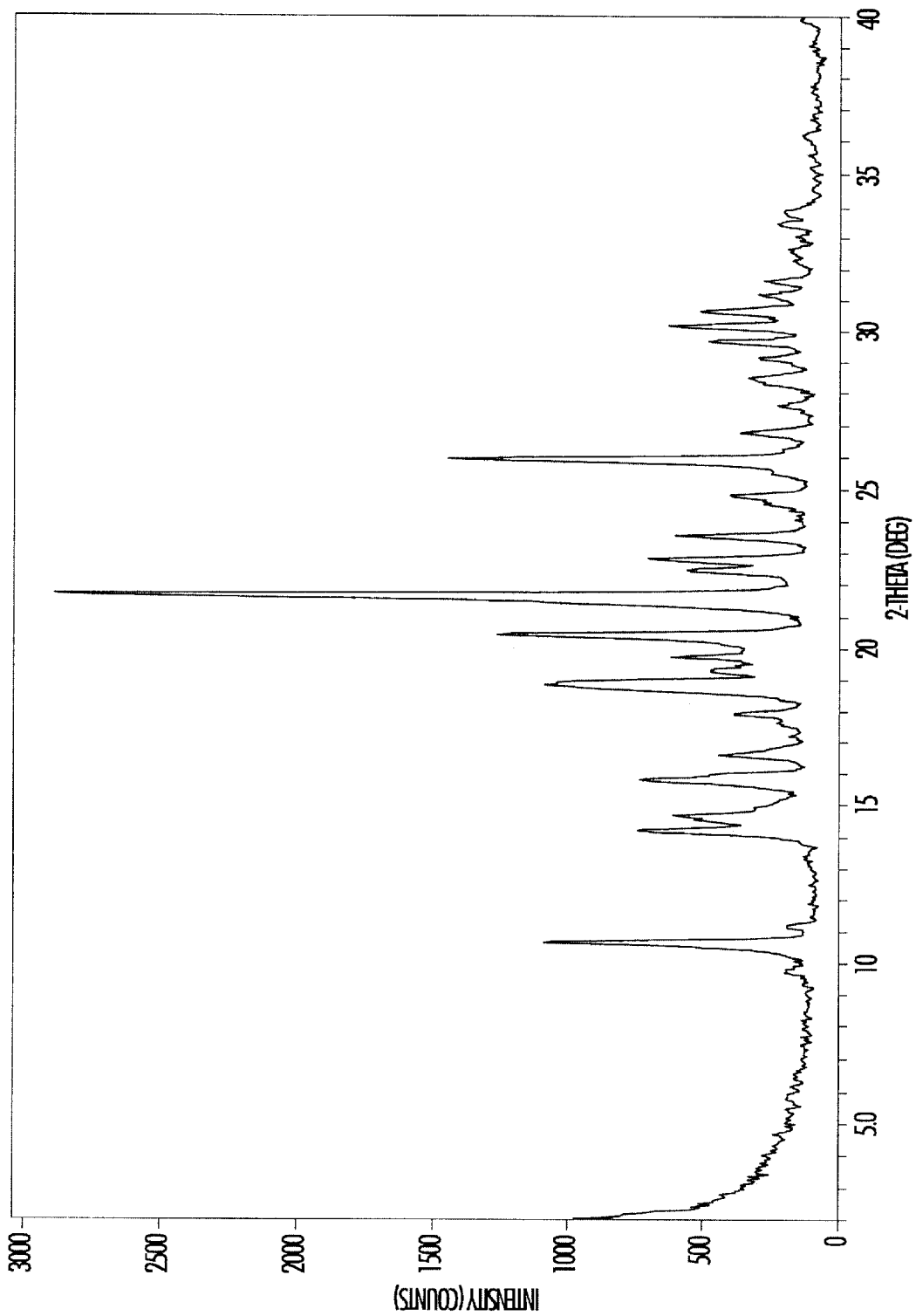
FIG. 10 illustrates an XRD pattern for Form B cilostazol.
Figure 11:
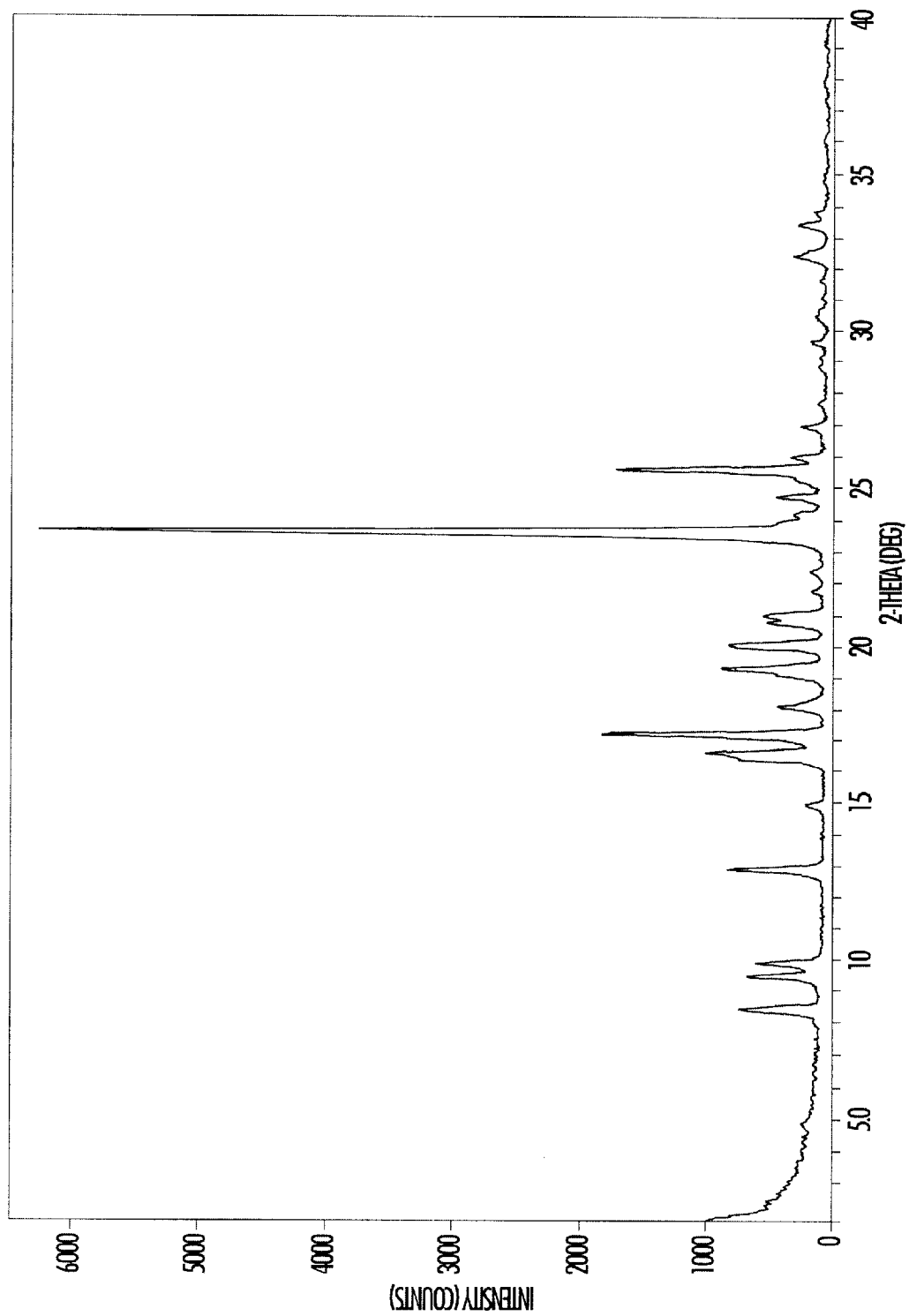
FIG. 11 illustrates an XRD pattern for Form C cilostazol.
Figure 12:
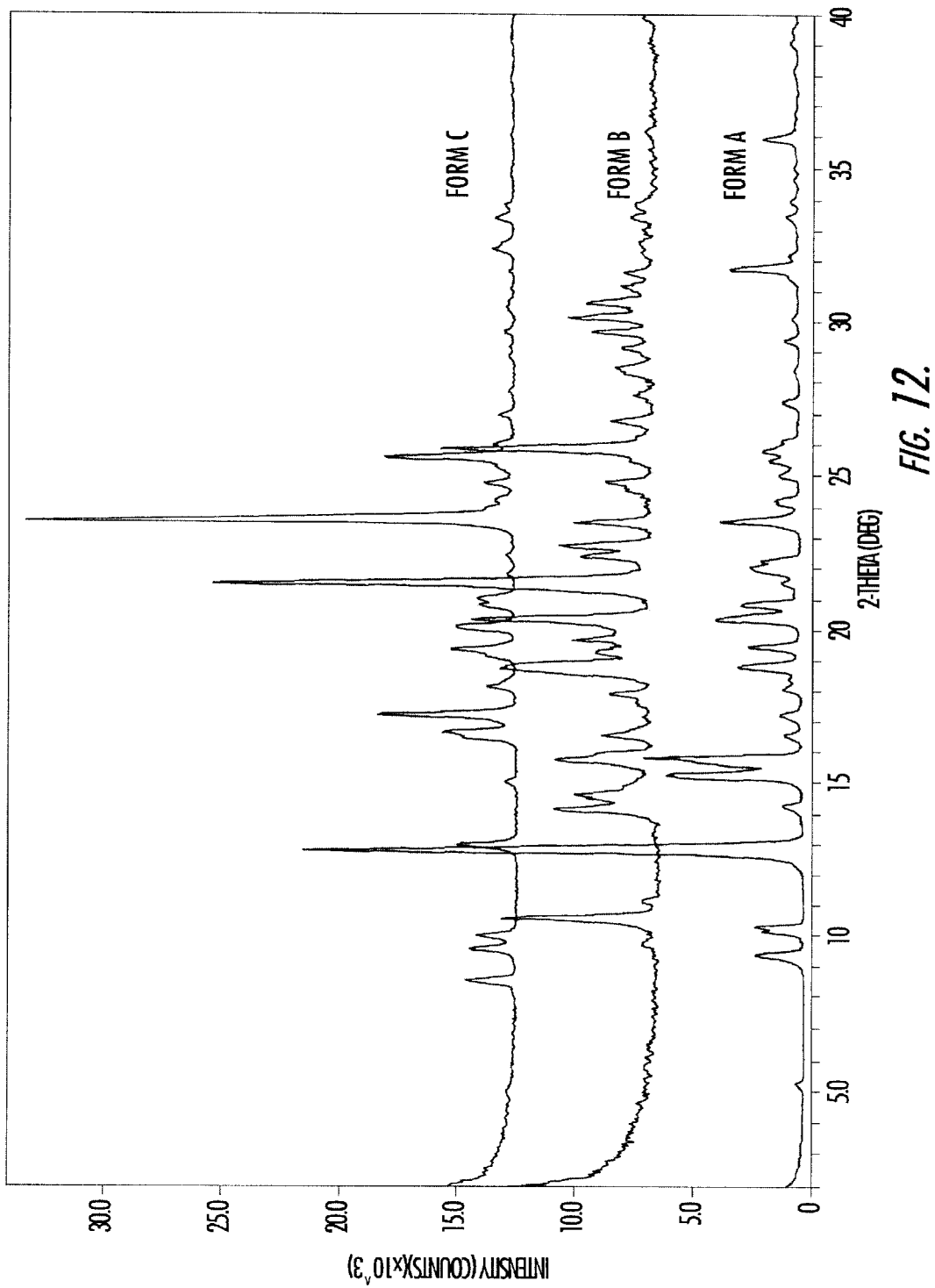
FIG. 12 illustrates an XRD pattern comparing Form A cilostazol, Form B cilostazol and Form C cilostazol.
Figure 13:
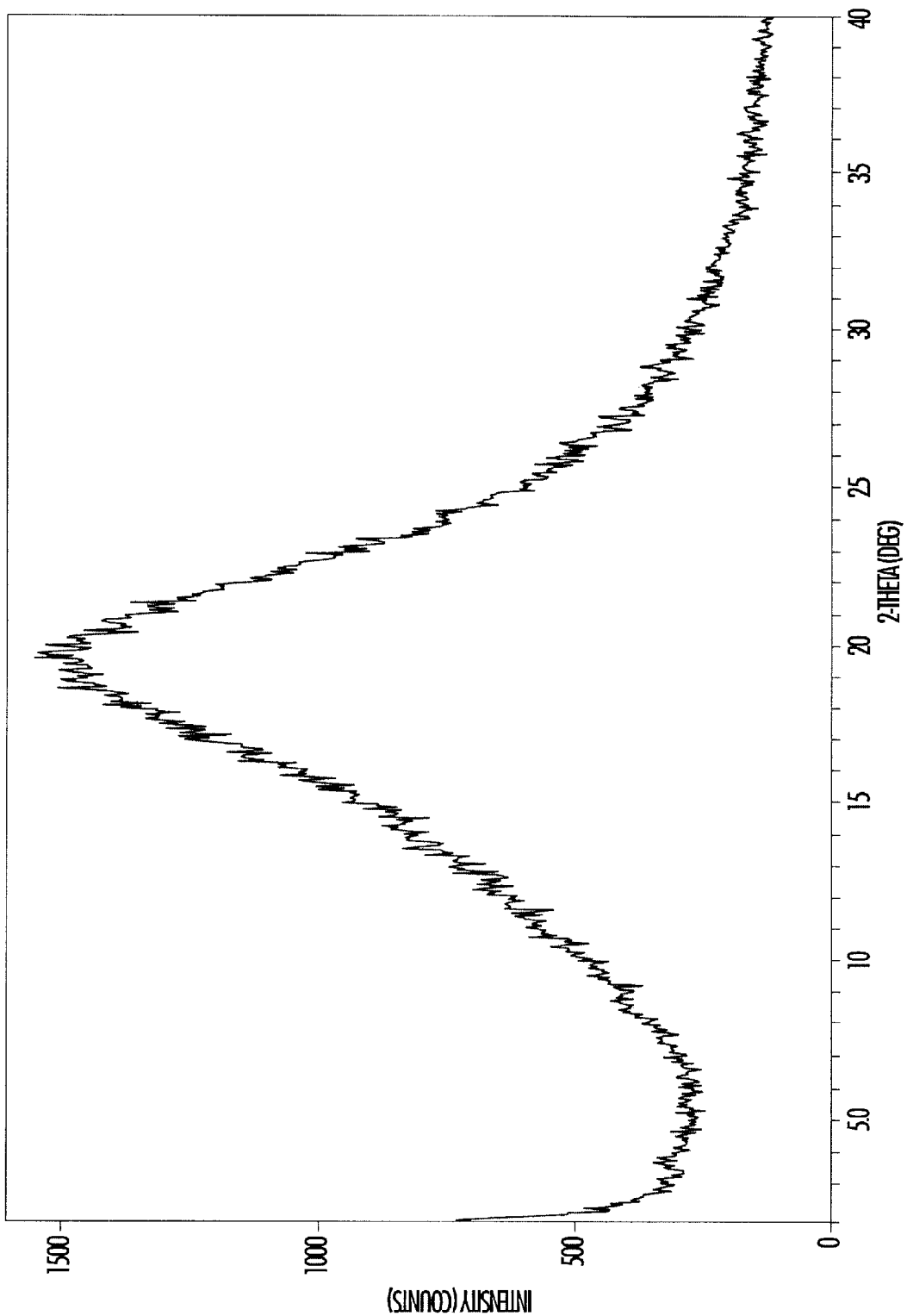
FIG. 13 illustrates an XRD pattern for amorphous cilostazol.

FIGS. 9, 10 and 11, the XRD patterns for Form A, Form B and Form C, respectively, are shown, with the three XRD patterns overlayed for comparison in FIG. 12. As seen in FIG. 12, the XRD patterns of Form A, Form B and Form C of cilostazol demonstrate three distinct crystalline forms of the cilostazol, evidencing pure Form B and pure Form C. Characterization of amorphous cilostazol was also performed, as seen in the XRD pattern for amorphous cilostazol in FIG. 13. XRD was performed using a Siemens D500 Diffractometer (Madison, Wis.). Samples were analyzed from 2–40° in 2θ at 2.4°/minute using CuKα (50kV, 30mA) radiation on a zero-background sample plate.

Tabulations of the peak positions from the X-ray powder patterns for Form A, Form B and Form C are listed in Tables 2, 3 and 4, respectively, below. It is well known by one of ordinary skill in the art that lot-to-lot variations of crystal shape and/or size, as well as variations among instruments and calibration of such instruments, can appear as preferred orientation in the X-ray powder diffraction patterns. This preferred orientation can be seen as variations in the relative intensities of the peaks, such variations in an amount of up to about 20%.

TABLE 2

X-Ray Powder Diffraction
Significant Peaks of Form A of Cilostazol

| 2-Theta (degrees) | d(Å) | Strength[1] | I % |
| --- | --- | --- | --- |
| 5.2 | 16.89 | vw | 1.6 |
| 9.4 | 9.40 | m | 9.3 |
| 10.3 | 8.59 | m | 9.4 |
| 12.9 | 6.86 | vs | 100.0 |
| 14.2 | 6.21 | w | 3.6 |
| 15.3 | 5.79 | s | 27.0 |
| 15.8 | 5.59 | s | 31.3 |
| 16.6 | 5.34 | w | 2.7 |
| 17.2 | 5.15 | w | 3.8 |
| 18.1 | 4.91 | w | 3.5 |
| 18.8 | 4.72 | m | 10.7 |
| 19.4 | 4.56 | m | 9.0 |
| 20.4 | 4.36 | m | 16.3 |
| 20.8 | 4.27 | m | 9.9 |
| 21.5 | 4.13 | vw | 1.2 |
| 22.0 | 4.03 | m | 9.9 |
| 22.2 | 3.99 | w | 7.6 |
| 23.5 | 3.78 | m | 15.7 |
| 24.2 | 3.67 | w | 4.4 |
| 25.0 | 3.56 | w | 3.6 |
| 25.5 | 3.49 | w | 5.7 |
| 25.8 | 3.46 | w | 7.0 |
| 25.9 | 3.43 | w | 4.3 |
| 27.4 | 3.25 | w | 3.2 |
| 28.3 | 3.15 | vw | 0.6 |
| 28.4 | 3.14 | vw | 0.9 |

TABLE 2-continued

X-Ray Powder Diffraction
Significant Peaks of Form A of Cilostazol

| 2-Theta (degrees) | d(Å) | Strength[1] | I % |
|---|---|---|---|
| 29.4 | 3.04 | w | 2.6 |
| 30.1 | 2.97 | vw | 1.1 |
| 31.7 | 2.82 | m | 13.3 |
| 32.1 | 2.78 | vw | 1.5 |
| 33.4 | 2.68 | vw | 1.9 |
| 33.9 | 2.64 | vw | 1.1 |
| 34.6 | 2.59 | vw | 0.6 |
| 35.0 | 2.56 | vw | 0.5 |
| 36.0 | 2.50 | vw | 6.5 |
| 38.2 | 2.35 | vw | 0.7 |
| 39.1 | 2.30 | vw | 1.2 |
| 39.5 | 2.28 | vw | 0.9 |

TABLE 3

X-Ray Powder Diffraction
Significant Peaks of Form B of Cilostazol

| 2-Theta (degrees) | d(Å) | Strength[1] | I % |
|---|---|---|---|
| 9.8 | 9.03 | w | 2.2 |
| 10.7 | 8.29 | s | 35.7 |
| 11.2 | 7.89 | vw | 1.9 |
| 13.4 | 6.61 | vw | 0.9 |
| 14.2 | 6.23 | s | 22.4 |
| 14.7 | 6.03 | m | 15.9 |
| 15.8 | 5.60 | s | 20.9 |
| 16.6 | 5.33 | m | 10.6 |
| 17.7 | 5.02 | w | 2.2 |
| 17.9 | 4.95 | m | 8.0 |
| 18.8 | 4.72 | s | 33.9 |
| 19.7 | 4.50 | w | 7.1 |
| 20.4 | 4.35 | s | 40.4 |
| 21.6 | 4.10 | vs | 100.0 |
| 22.4 | 3.96 | m | 13.7 |
| 22.8 | 3.90 | m | 20.0 |
| 23.5 | 3.78 | m | 17.2 |
| 24.7 | 3.61 | w | 5.3 |
| 24.8 | 3.58 | m | 9.9 |
| 25.9 | 3.43 | s | 48.0 |
| 26.8 | 3.32 | m | 8.1 |
| 27.7 | 3.22 | w | 4.0 |
| 28.5 | 3.13 | w | 7.1 |
| 29.2 | 3.06 | w | 4.7 |
| 29.7 | 3.01 | m | 10.1 |
| 30.2 | 2.96 | m | 12.9 |
| 30.7 | 2.91 | m | 8.7 |
| 31.2 | 2.86 | w | 6.7 |
| 31.6 | 2.83 | w | 4.2 |
| 32.3 | 2.77 | vw | 1.7 |
| 32.6 | 2.74 | w | 2.2 |
| 33.0 | 2.71 | vw | 0.9 |
| 33.5 | 2.68 | w | 4.3 |
| 33.8 | 2.65 | w | 3.8 |

TABLE 4

X-Ray Powder Diffraction
Significant Peaks of Form C of Cilostazol

| 2-Theta (degrees) | d(Å) | Strength[1] | I % |
|---|---|---|---|
| 5.0 | 17.51 | w | 0.8 |
| 8.6 | 10.22 | s | 10.1 |
| 9.7 | 9.12 | vw | 9.3 |
| 10.1 | 8.75 | vw | 8.3 |
| 13.1 | 6.78 | s | 12.3 |
| 15.1 | 5.85 | m | 2.3 |
| 16.7 | 5.29 | s | 15.1 |
| 17.3 | 5.12 | m | 27.7 |
| 18.2 | 4.86 | w | 5.6 |
| 19.4 | 4.56 | m | 12.3 |
| 20.2 | 4.40 | s | 11.4 |
| 20.9 | 4.25 | w | 6.7 |
| 21.1 | 4.21 | w | 7.2 |
| 21.9 | 4.07 | vw | 1.1 |
| 22.5 | 3.95 | vw | 1.4 |
| 23.7 | 3.75 | vs | 100.0 |
| 24.3 | 3.66 | w | 2.5 |
| 24.8 | 3.58 | w | 4.8 |
| 25.7 | 3.46 | s | 25.9 |
| 26.1 | 3.41 | w | 4.0 |
| 27.1 | 3.29 | w | 3.0 |
| 27.8 | 3.21 | vw | 1.0 |
| 29.0 | 3.08 | vw | 0.9 |
| 29.2 | 3.05 | vw | 0.6 |
| 29.8 | 3.00 | vw | 1.7 |
| 30.5 | 2.92 | vw | 1.4 |
| 31.7 | 2.82 | vw | 0.7 |
| 32.5 | 2.76 | w | 4.1 |
| 33.5 | 2.68 | w | 3.6 |
| 33.9 | 2.64 | vw | 1.6 |
| 34.9 | 2.57 | vw | 0.6 |
| 36.2 | 2.48 | vw | 0.5 |
| 37.4 | 2.40 | vw | 0.3 |
| 38.0 | 2.36 | vw | 0.5 |
| 39.2 | 2.30 | vw | 0.5 |

[1]vs = very strong (>50%), s strong (>20%), m = moderate (8–20%), w = weak (2–8%), vw = very weak (<2%)

The XRD peaks shown in Table 2, demonstrated that the significant peaks of Form A (greater than 8%) are typically located at two-theta (2θ) angles if about 9.4, 10.3, 12.9, 15.3, 15.8, 18.8, 19.4, 20.4, 20.8, 22.0, 23.5 and 31.7°. For Form B, the significant XRD peaks (shown in Table 3) are at two-theta (2θ) angles of about 10.7, 14.2, 14.7, 15.8, 16.6, 17.9, 18.8, 20.4, 21.6, 22.4, 22.8, 23.5, 24.8, 25.9, 26.8, 29.7, 30.2, and 30.7°. For Form C, the significant XRD peaks (shown in Table 4) are at two-theta (2θ) angles of about 8.6, 9.7, 10.1, 13.1, 16.7, 17.3, 19.4, 20.2, 23.7 and 25.7°.

Figure 14:
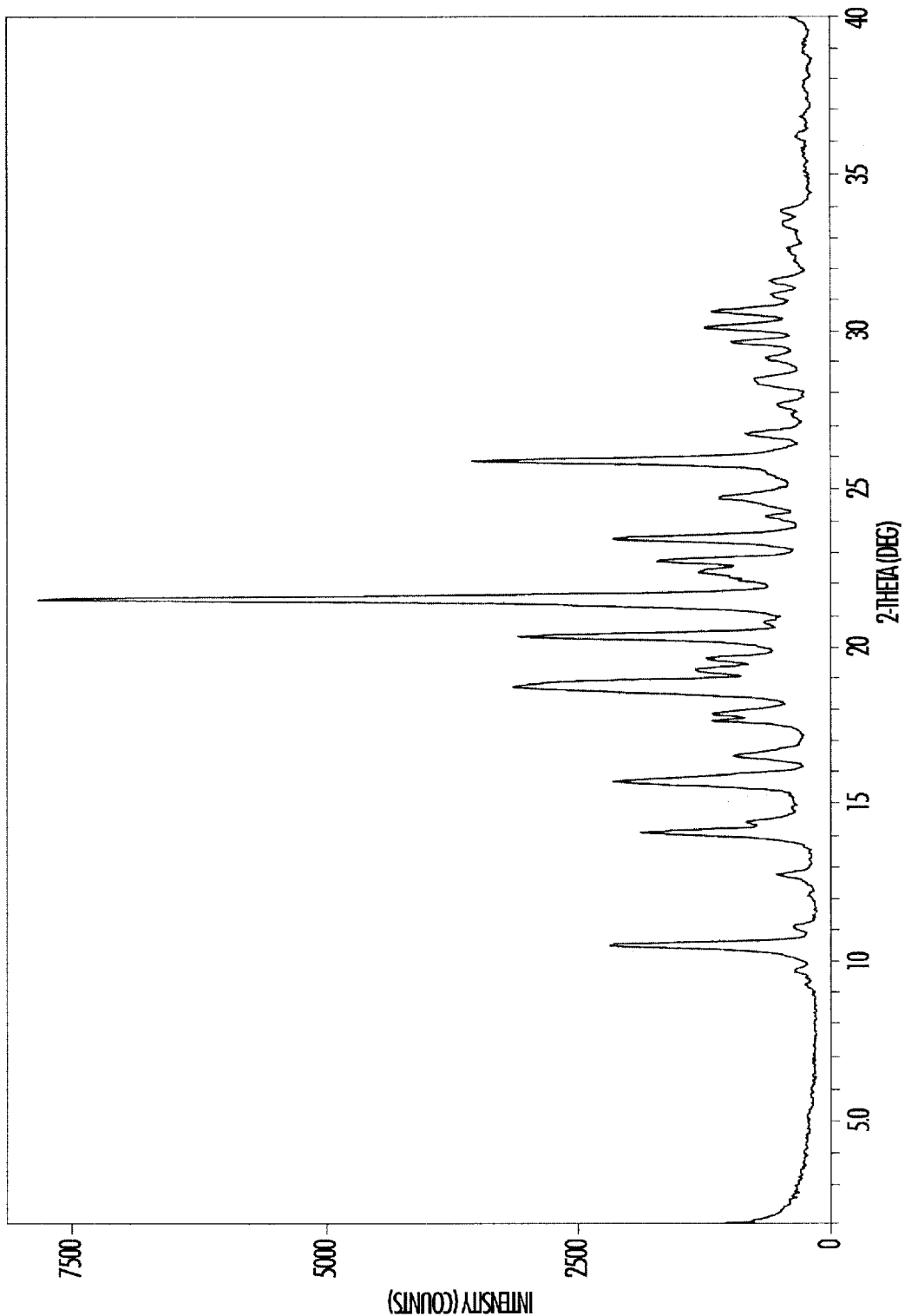
FIG. 14 illustrates an XRD pattern for the combination of Form A cilostazol (minor) and Form B cilostazol (major)

The XRD pattern for the combination of a minor (approximately 10%) amount of Form A of cilostazol and a major (approximately 90%) amount of Form B of cilostazol is shown in FIG. 14.

Figure 15:
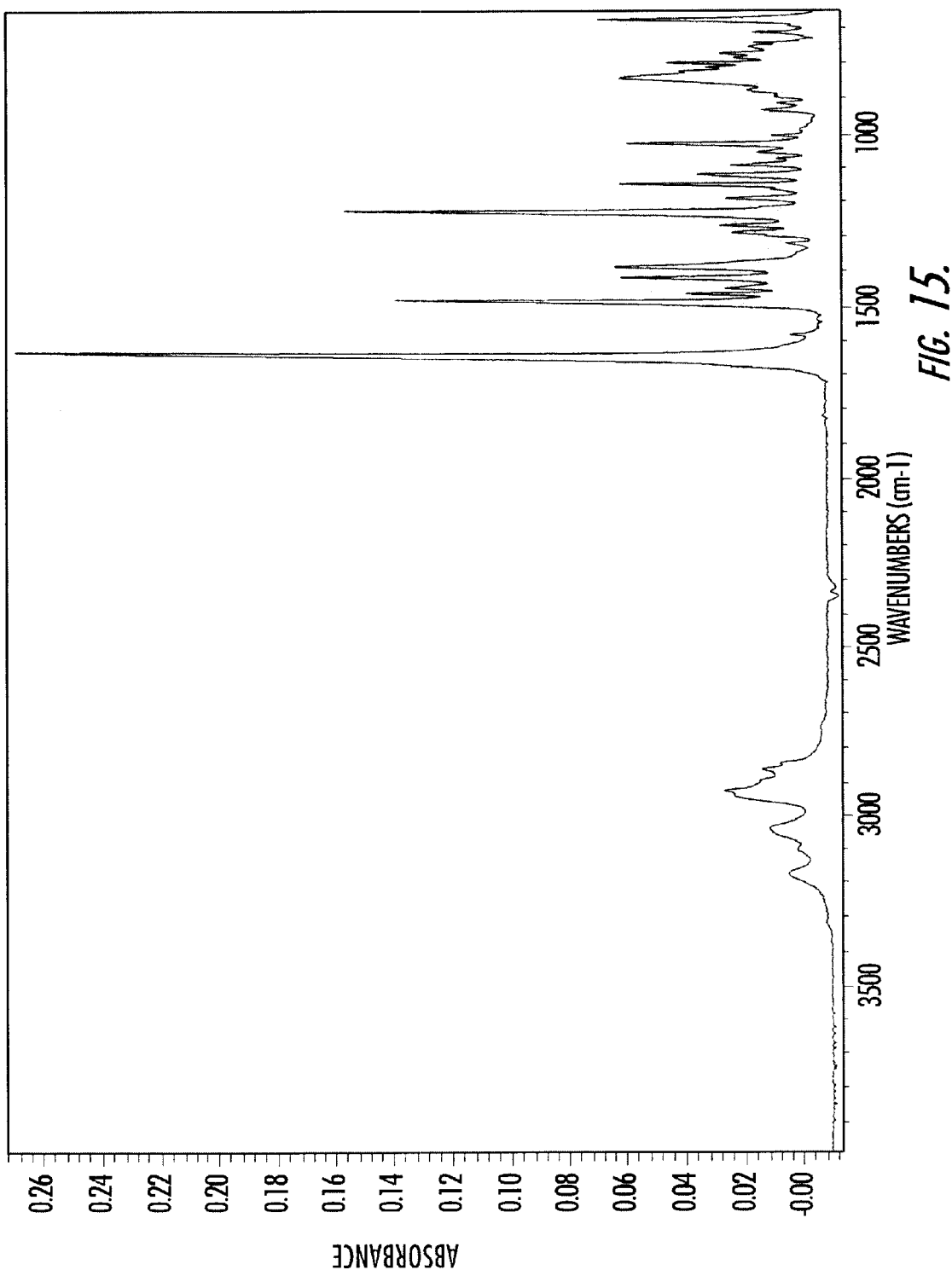
FIG. 15 illustrates a Fourier Transform Infrared Spectroscopy (FTIR) spectrum for Form A cilostazol.
Figure 16:
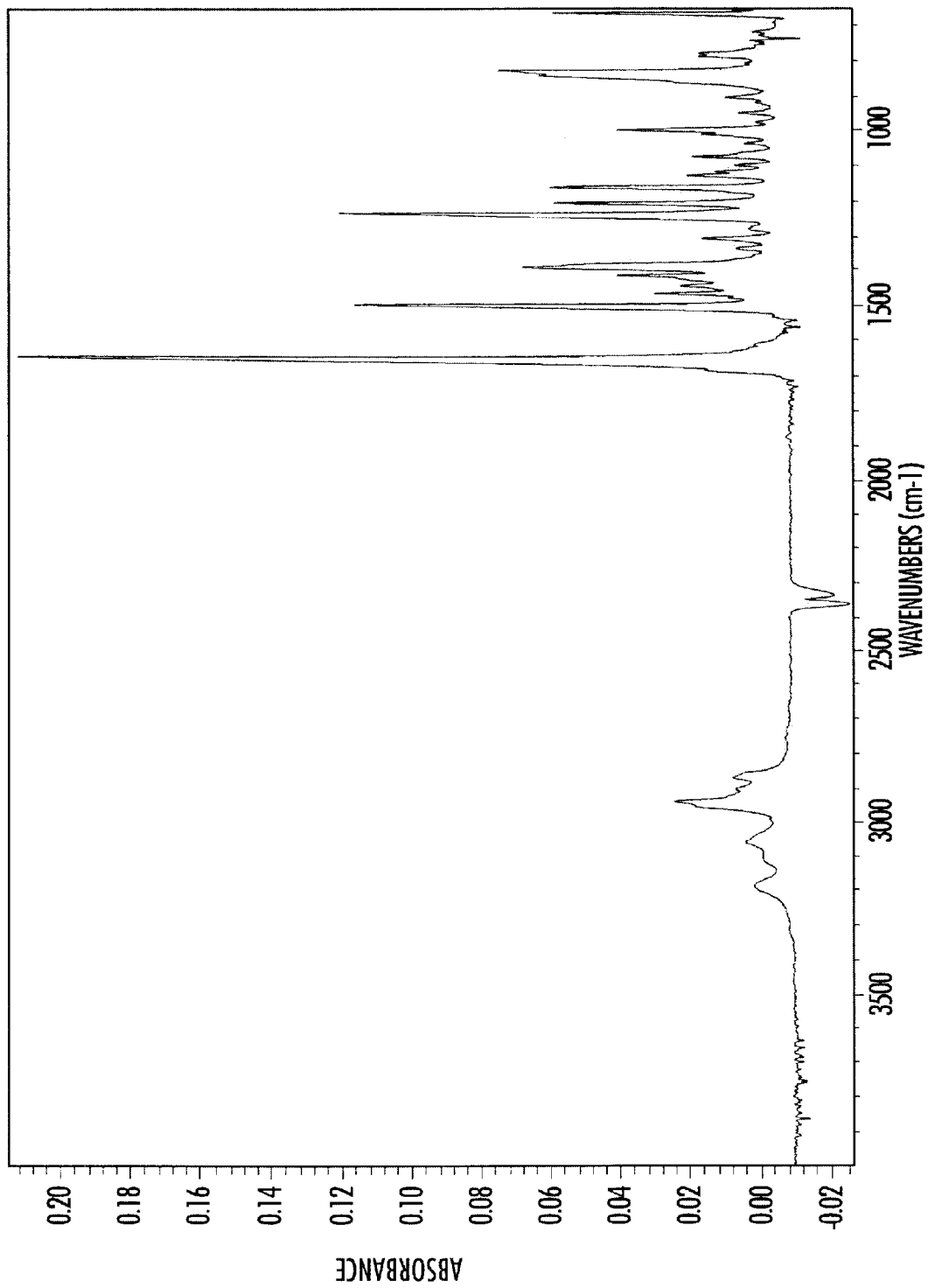
FIG. 16 illustrates a FTIR spectrum for Form B cilostazol.
Figure 17:
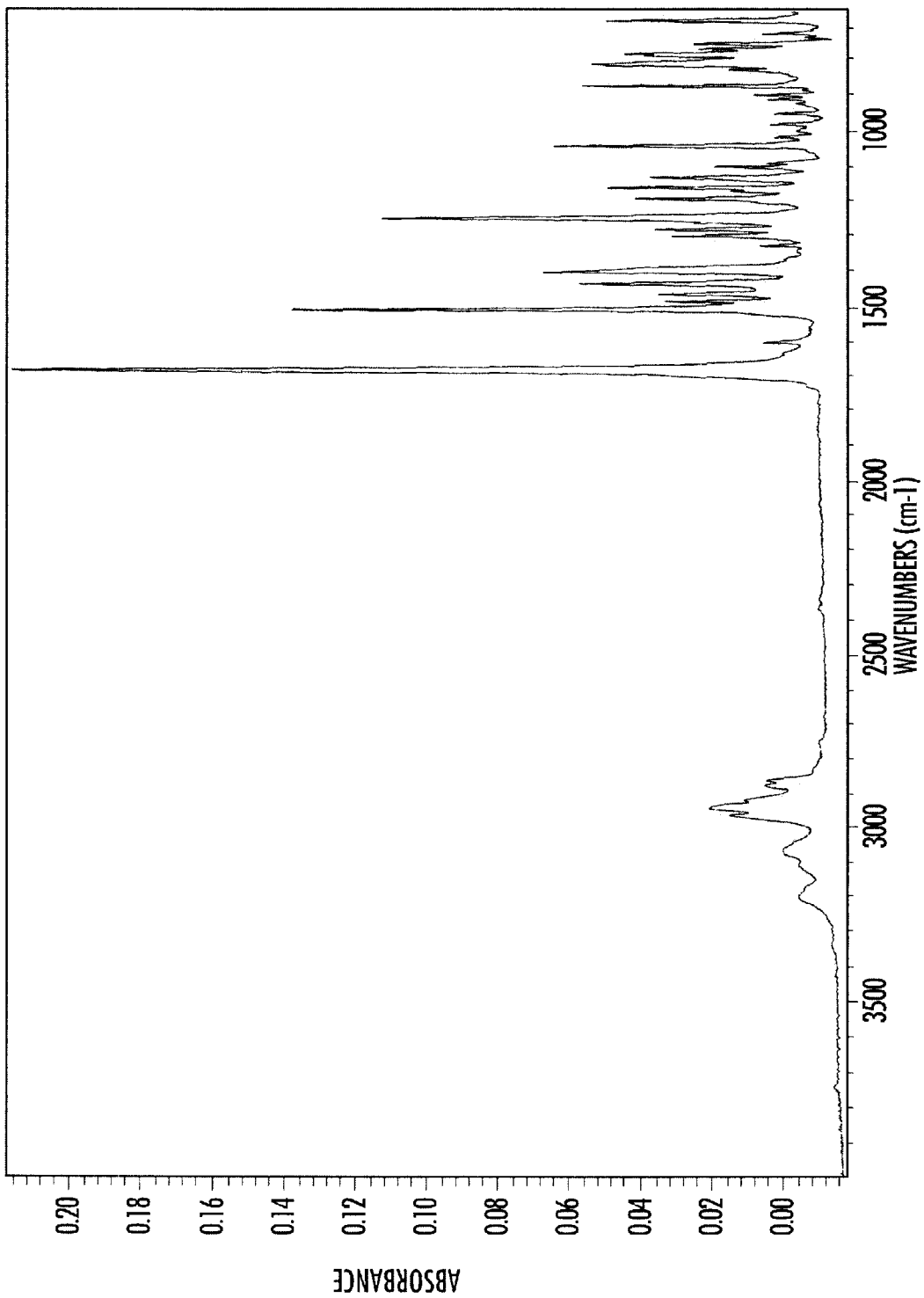
FIG. 17 illustrates a FTIR spectrum for Form C cilostazol.
Figure 18:
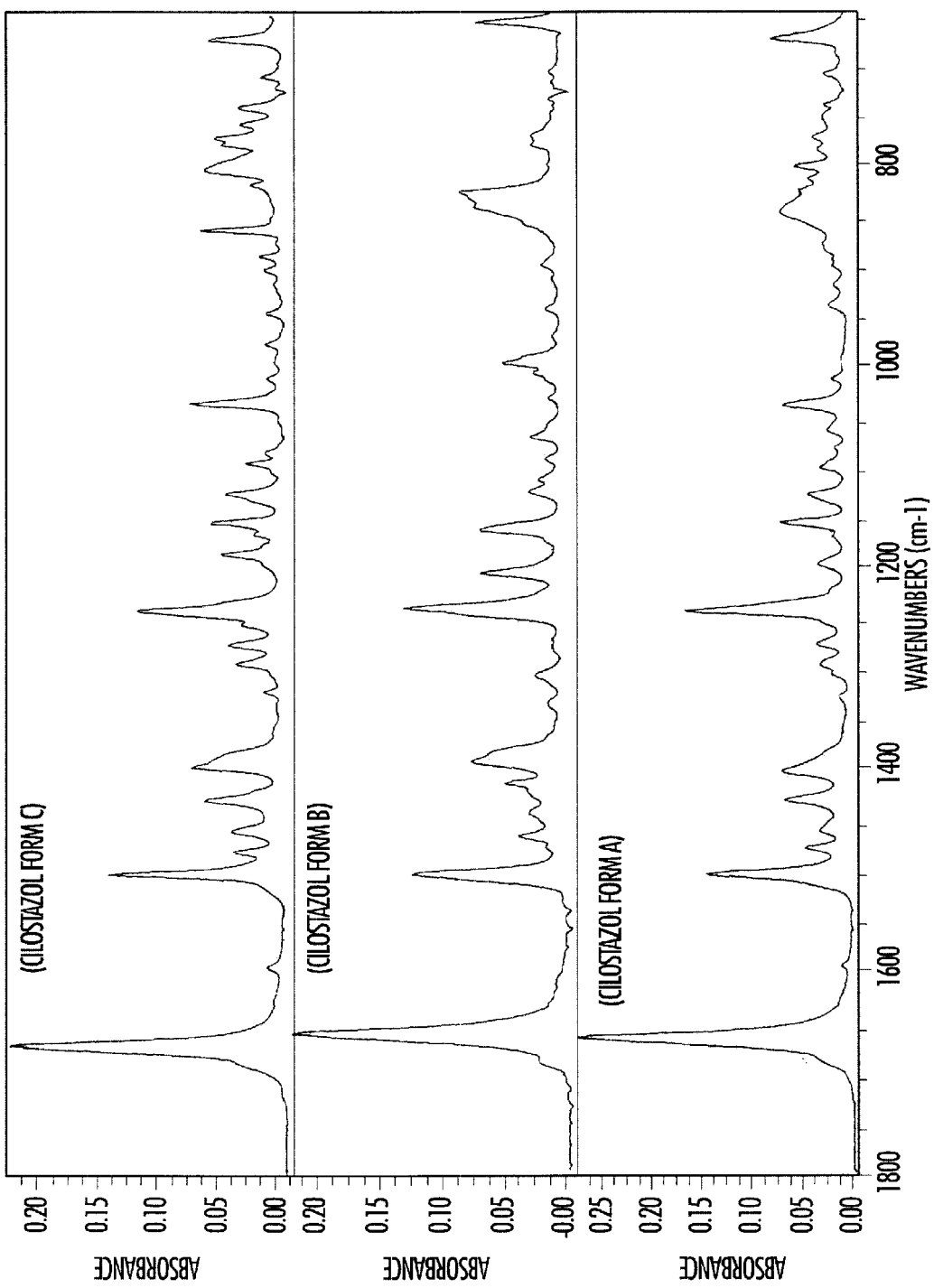
FIG. 18 illustrates a FTIR spectrum overlaying Form A cilostazol, Form B cilostazol and Form C cilostazol.
Figure 19:
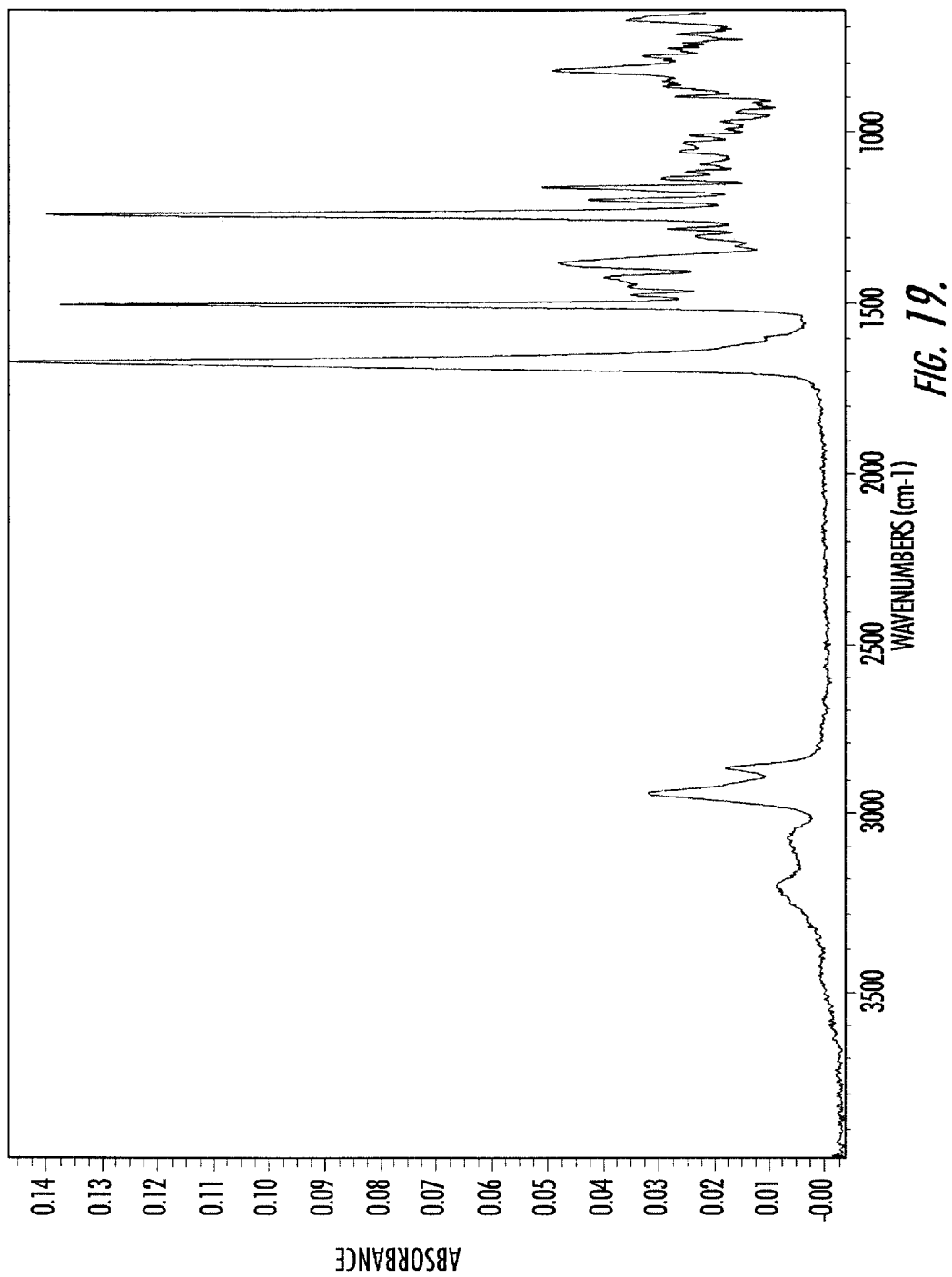
FIG. 19 illustrates a FTIR spectrum for amorphous cilostazol.
Figure 20:
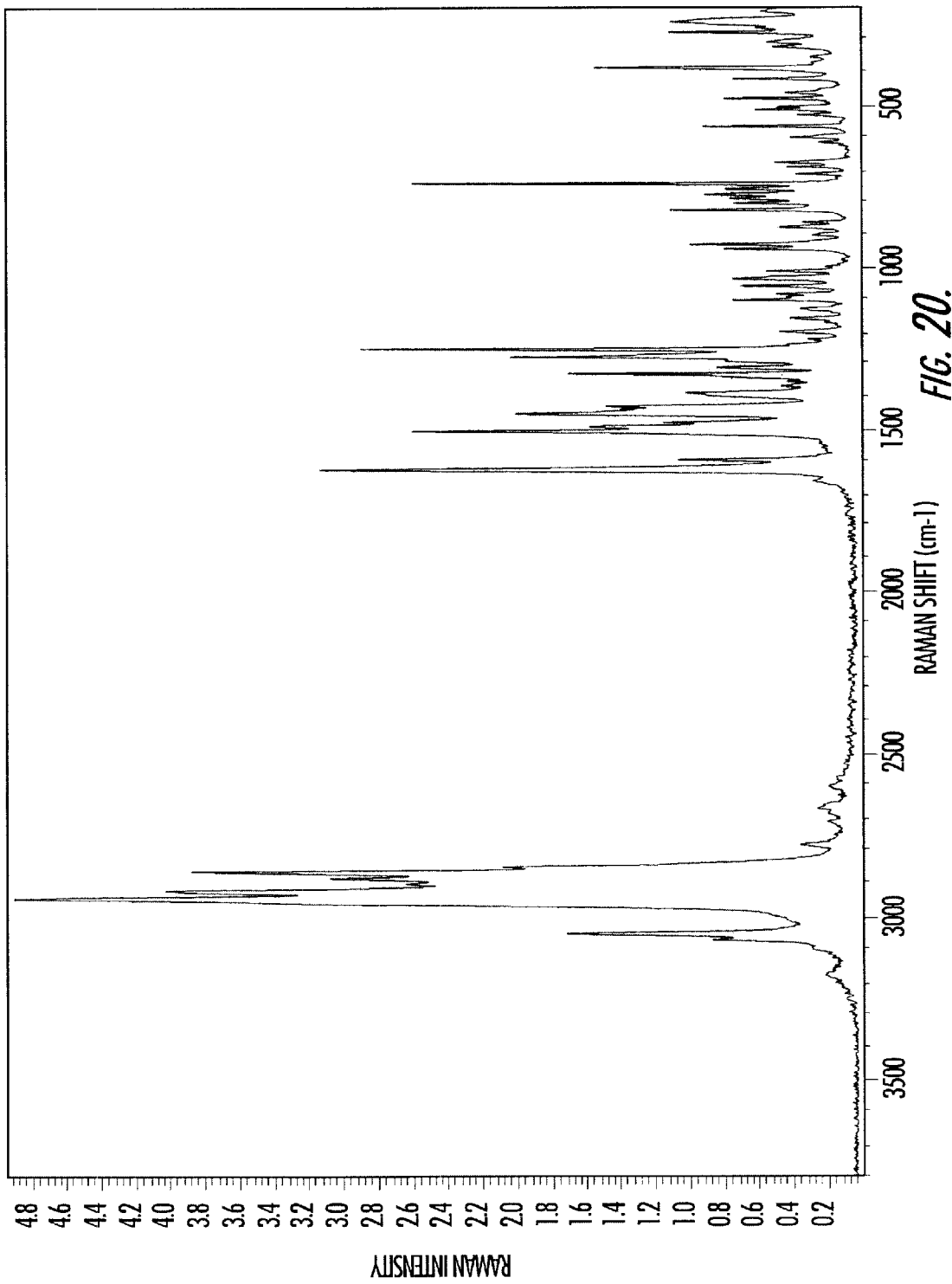
FIG. 20 illustrates a Fourier Transform Raman Spectroscopy (FT-Raman) spectrum for Form A cilostazol.
Figure 21:
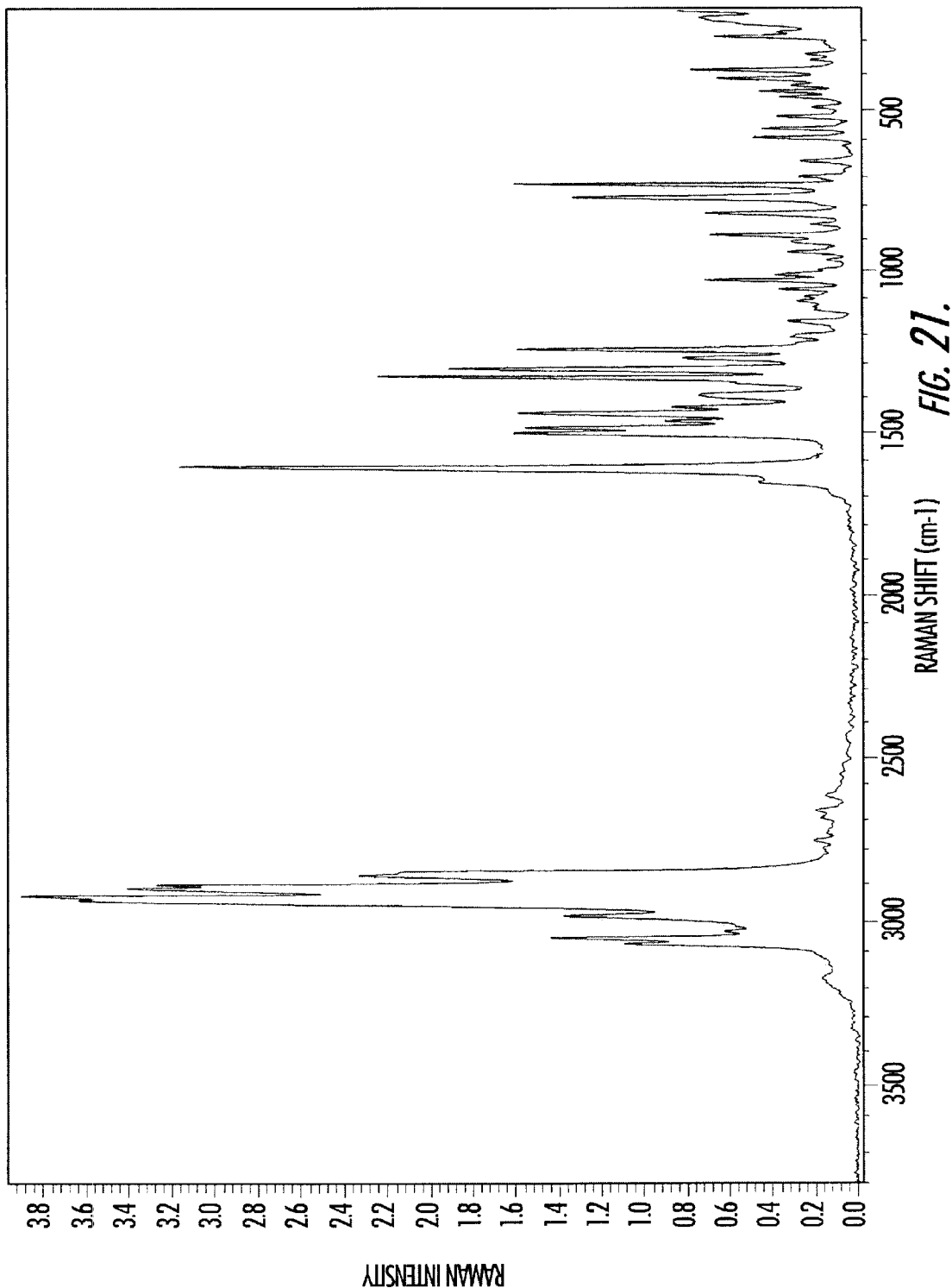
FIG. 21 illustrates a FT-Raman spectrum for Form B cilostazol.
Figure 22:
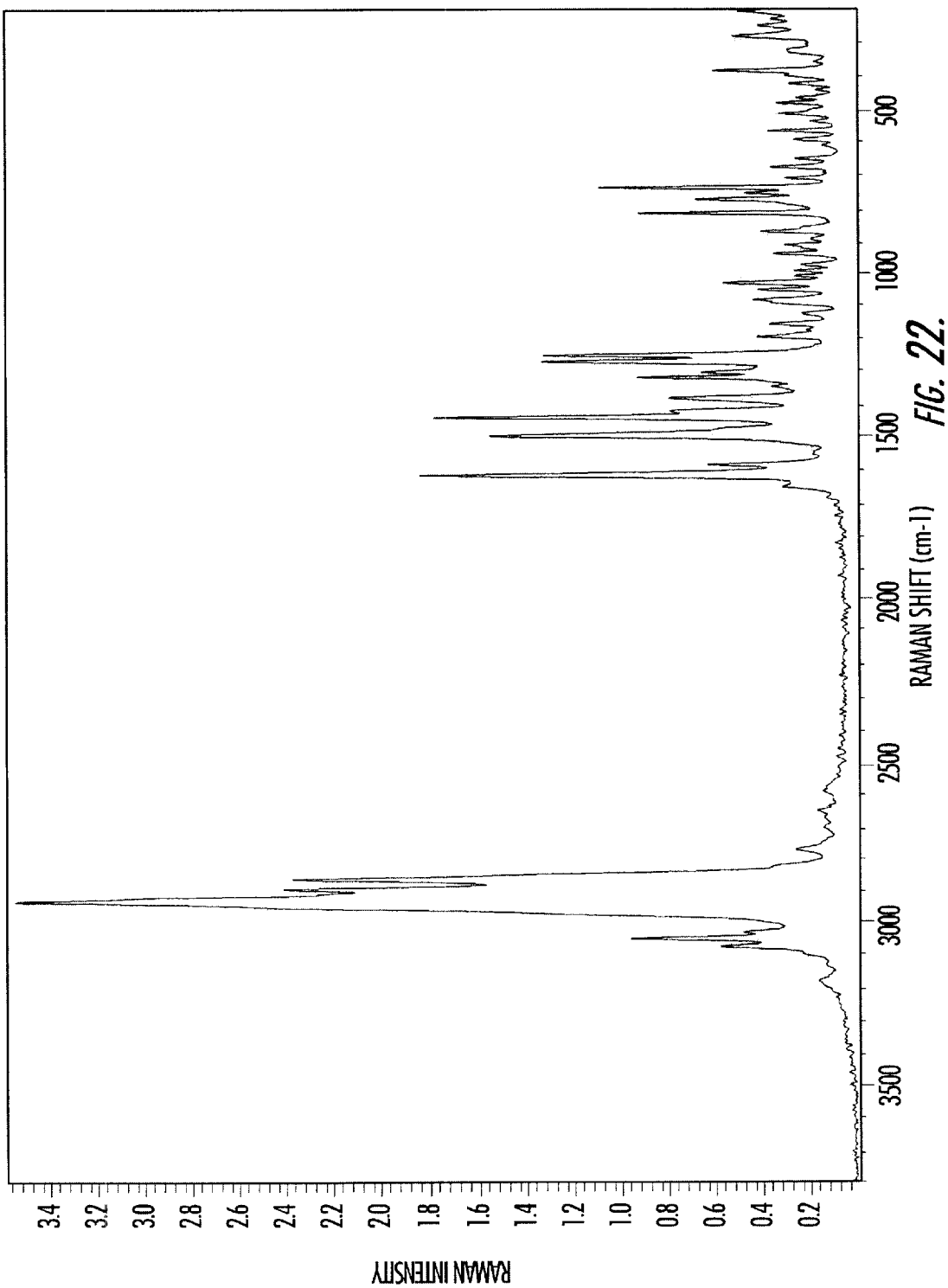
FIG. 22 illustrates a FT-Raman spectrum for Form C cilostazol.
Figure 23:
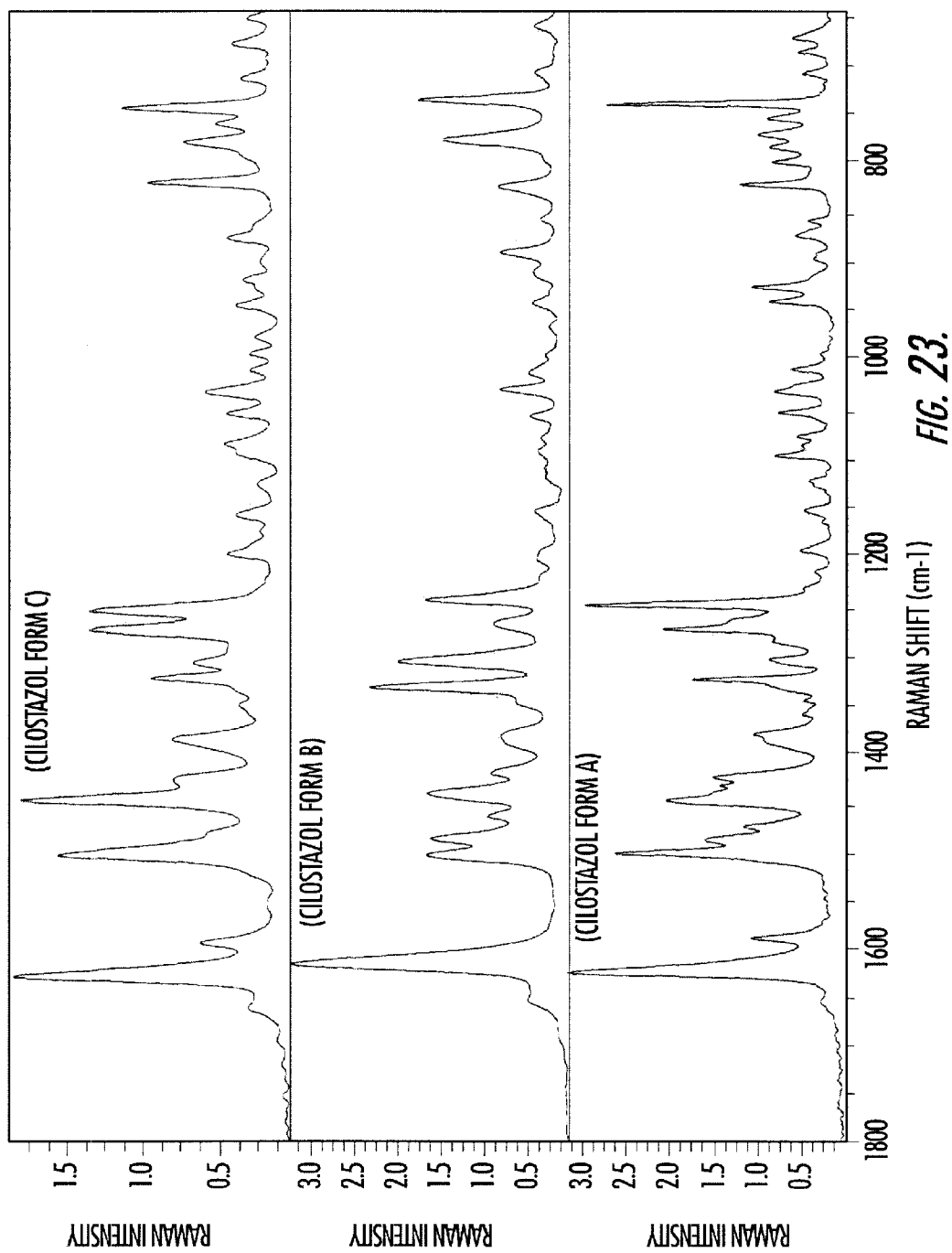
FIG. 23 illustrates a FT-Raman spectrum for Form A cilostazol, Form B cilostazol and Form C cilostazol.
Figure 24:
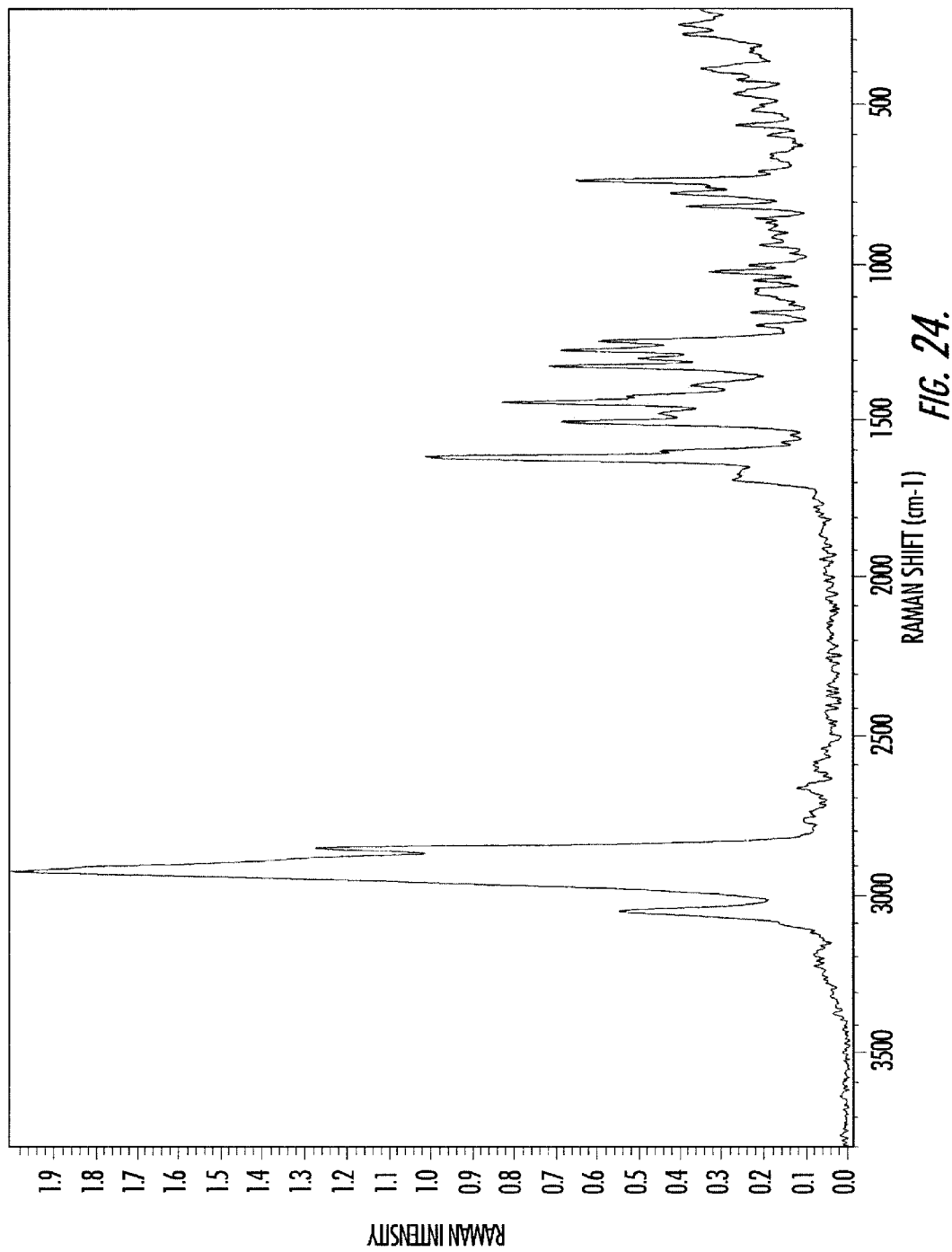
FIG. 24 illustrates a FT-Raman spectrum for amorphous cilostazol.

The FTIR spectrum for Form A, Form B and Form C, are shown in FIGS. 15, 16, and 17, respectively and an overlay of the three spectra are shown in FIG. 18. The FTIR spectrum for amorphous cilostazol is shown in FIG. 19. FTIR was performed using a Nicolet Nexus 670 FTIR spectrometer with a Micro-FTIR attachment (Silicon ATR). Analysis was generally performed on neat samples at 4 cm$^{-1}$ resolution, collecting 64 scans from 4000–650 cm$^{-1}$. The major bands of the FTIR spectra of Form A, Form B, and Form C are tabulated in Table 5, below:

TABLE 5

Major FTIR peaks of Form A, Form B, Form C and Amorphous Cilostazol (cm$^{-1}$)

| Form A of cilostazol | Form B of cilostazol | Form C of cilostazol | Amorphous cilostazol |
|---|---|---|---|
| 3180 | 3181 | 3191 | 3210 |
| 3046 | 3054 | 3056 | 3063 |
| 2937 | 2940 | 2938 | 2934 |
| 2872 | 2868 | 2870 | 2861 |
| 1667 | 1662 | 1674 | 1672 |
| 1505 | 1504 | 1504 | 1504 |
| 1431 | 1443 | 1430 | 1421 |
| 1402 | 1393 | 1398 | 1381 |
| 1244 | 1240 | 1243 | 1240 |
| 1197 | 1205 | 1187 | 1195 |
| 1156 | 1162 | 1154 | 1156 |
| 1128 | 1124 | 1126 | 1130 |
| 1039 | 1030 | 1036 | 1026 |
| 846 | 842 | 864 | 863 |
| 675 | 658 | 674 | 670 |

The polymorphic forms of cilostazol are further characterized in FIGS. 20, 21, 22, and 24 for Form B, Form C, and amorphous cilostazol respectively. FT-Raman was performing using a Nicolet Nexus 670 FTIR spectrometer with a FT-Raman attachment. Samples were generally analyzed neat at 8 cm$^{-1}$ resolution, collecting 100 scans from 3800–100 cm$^{-1}$ with a laser wattage of approximately 1 W. Major spectral bands of the FT-Raman for the Form A, Form B, Form C and amorphous cilostazol are listed in Table 6, below:

TABLE 6

Major FT-Raman peaks of Form A, Form B, Form C (cm$^{-1}$) and Amorphous Cilostazol

| Form A of cilostazol | Form B of cilostazol | Form C of cilostazol | Amorphous cilostazol |
|---|---|---|---|
| 3056 | 3054 | 3051 | 3059 |
| 2954 | 2941 | 2939 | 2940 |
| 2927 | 2914 | 2900 | 2905 |
| 2871 | 2868 | 2869 | 2861 |
| 1626 | 1616 | 1627 | 1618 |
| 1592 | — | 1593 | 1594 |
| 1505 | 1506 | 1503 | 1506 |
| 1452 | 1443 | 1447 | 1445 |
| 1428 | 1422 | 1425 | 1420 |
| 1385 | 1386 | 1386 | 1387 |
| 1329 | 1334 | 1324 | 1328 |
| 1309 | 1308 | 1308 | 1303 |
| 1278 | 1271 | 1274 | 1277 |
| 1253 | 1246 | 1255 | 1247 |
| 1056 | 1057 | 1052 | 1053 |
| 1034 | 1030 | 1031 | 1028 |
| 1012 | 1013 | 1008 | 1007 |
| 875 | 890 | 873 | 872 |
| 861 | 856 | 861 | 858 |
| 824 | 824 | 817 | 819 |
| 773 | 776 | 777 | 776 |
| 741 | 735 | 740 | 739 |
| 675 | 660 | 676 | 675 |
| 594 | 590 | 592 | 592 |
| 565 | 562 | 566 | 561 |
| 527 | 525 | 535 | 530 |
| 420 | 409 | 418 | 418 |
| 384 | 383 | 379 | 384 |
| 277 | 280 | 276 | 275 |

Figure 25:
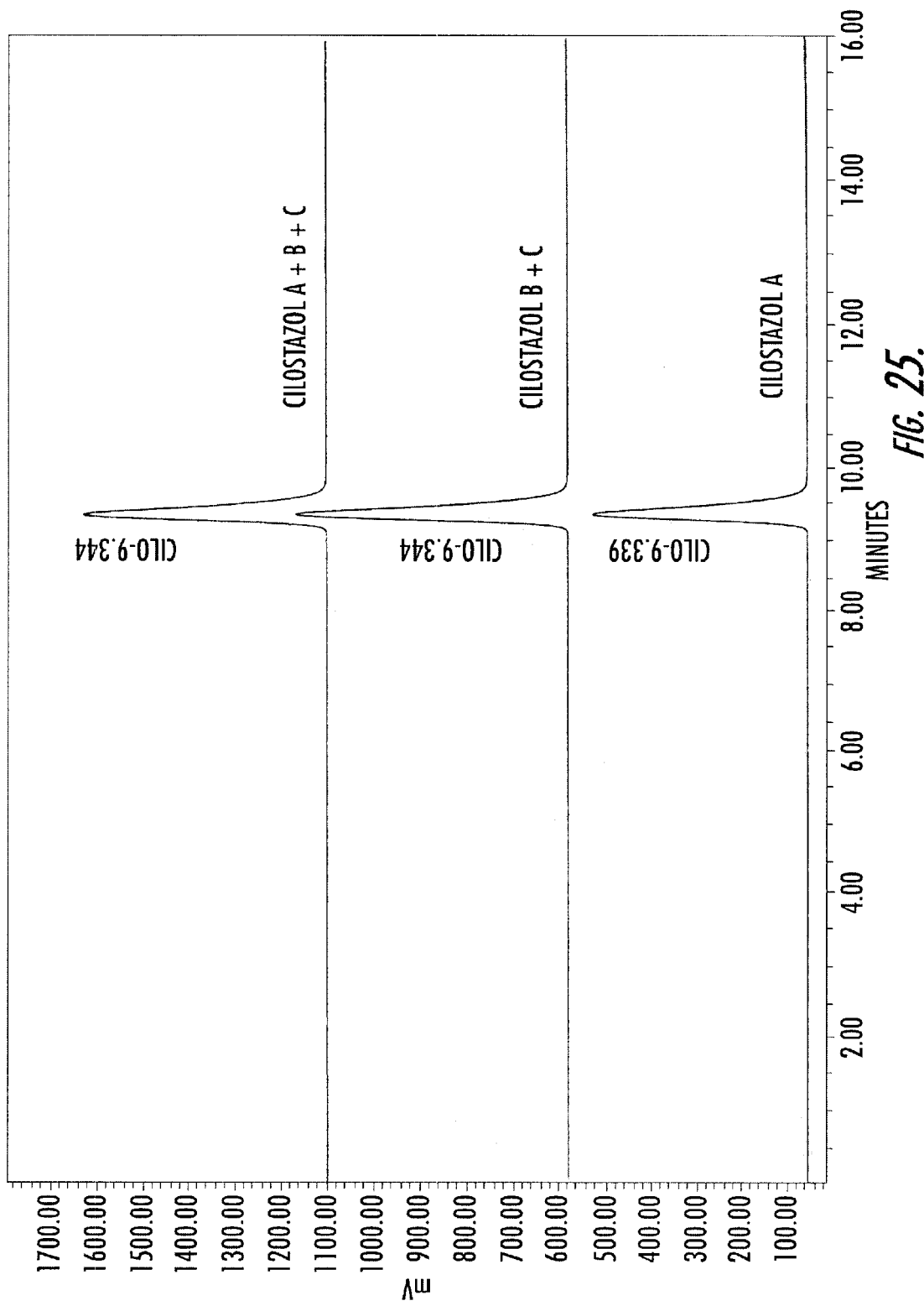
FIG. 25 illustrates a HPLC chromatographic overlay comparing various combinations of crystalline polymorphic forms of cilostazol.

The HPLC Chromatogram of Form A was overlayed with the chromatograms of a combination of polymorphic Form B and Form C, and the chromatogram of a combination of polymorphic Form A with Form B and Form C as shown in FIG. 25. This overlay demonstrates the purity and identity of each polymorphic combination to be as the same compound in solution (i.e., no degradation occurred in the thermal processing of the cilostazol) with a total amount of impurities of less than about 0.1% in each polymorphic combination.

Accordingly, the amorphous, Form B, and Form C polymorphic forms of cilostazol have been characterized as distinct from Form A, and from each other. X-ray single crystal structural analysis, DSC, XRD, FTIR, and/or FT-Raman confirm the existence of the novel Form B of cilostazol, Form C, and amorphous cilostazol, and other various combinations of polymorphic forms of the present invention.

In preparing amorphous cilostazol, any polymorphic form or combination of polymorphs of cilostazol (preferably Form A) is used as a starting material. The starting material is heated sufficiently for melting. Typically, when the heating rate is held constant at about 10° C./minute Form A of cilostazol melts at a temperature at about 160° C. Thus, temperatures from about 170° C. or greater (preferably up to about 200° C.) are used to ensure complete melt of the cilostazol starting material. Excessive temperatures that may alter the chemical characteristics, (e.g., cause degradation) of the cilostazol molecules are not used. As such, representative melting temperatures range from about 170° C. to about 200° C. Heating rates include any controllable heating process for complete melting of the cilostazol starting material. Representative static or variable heating rates include, for example, from about 5° C. per minute, 10° C. per minute, 15° C. per minute, 50° C. per minute, and other such rates. An inert atmosphere, such as for example, a nitrogen atmosphere or, preferably, nitrogen purge, should be used to reduce or eliminate potential oxidative reactions during the melting of the cilostazol.

The melted cilostazol is cooled from its molten state to about ambient temperature or below to provide amorphous cilostazol. The cooling steps described herein were all run at a cooling rate at about 10° C./minute using the aforementioned Julabo FT900 intercooler chiller. The cilostazol sample should be maintained free of debris, such as dust and other foreign material and contaminates, and/or mechanical shock that would induce nucleation sites within the cilostazol sample. Rates of cooling are controlled to minimize thermal shock and performed in a manner to minimize contaminates and/or mechanical shock to the cilostazol which could induce nucleation sites which can induce crystallization. Typically, this will result in the formation Form A cilostazol. Representative cooling rates include, for example, from about 1° C. per minute, 5° C. per minute, 10° C. per minute, 15° C. per minute, 50° C. per minute, and other such rates.

The identical steps of melting and cooling as described above are used for forming amorphous cilostazol are used for preparing Form B and/or Form C of cilostazol.

The samples are cooled for the formation of Form B and/or Form C, by reducing the temperature of the sample to about or below the glass transition temperature of cilostazol (about 32° C.). Cooling such samples only to temperatures greater than about 32° C. can provide such polymorph formation, primarily Form B, but the resulting material typically is of significantly lower purity. Because this cooling step can significantly affect the purity of the polymorph(s) formed in subsequent steps, the temperature of the melted cilostazol is cooled to a temperature of about 0° C. or less, and more preferably to temperatures of from about 0° C. to about −20° C. A preferred cooling rate is about 10° C./minute.

The next step, reheating of the cooled sample, is the step that controls the formation of Form B, Form C, and various combinations of the polymorphic forms of cilostazol. Typically, three primary variables are responsible for such formation including: heating rate, maximum temperature (heating temperature), and holding time (collectively, the "heating variables"). One of ordinary skill in the art will recognize that the change of one heating variable will affect one or both of the other heating variables. It is important to note that maximum temperature refers to the heating temperature of the entire, respective sample, and hold time commences upon such entire sample reaching the desired heating temperature. For example, when the heating rate is held constant, an increase in the heating temperature will typically permit a reduction in the hold time while the same, desired polymorph or combination of polymorphs, is formed. Accordingly, the teachings herein are intended to demonstrate the preparation of the cilostazol polymorphs of the present invention but, in no way, should be construed as limiting to the scope and breadth of the present invention.

Heating rates are controlled in a manner to systematically impart energy into the cilostazol sample. Representative heating rates include from about 1° C. per minute, 5° C. per minute, 10° C. per minute, 20° C. per minute, 50° C. per minute, and the like. However, it is best to maintain the heating rate constant at a rate of about 5° C. to about 20° C. per minute, and more preferably at about 10° C. per minute.

For the preparation of Form B, when holding the heating rate constant, as temperatures are increased, the percent of Form B is generally increased compared to other polymorphic forms as determined by the DSC methods taught herein. For example, when the cooled sample is heated to a temperature of 80° C., the sample primarily remains amorphous cilostazol, generally, because the energy required to form crystalline polymorphic cilostazol is insufficient, particularly when the heating hold time is negligible. Similarly, holding the heating rate constant and a hold time of about zero minutes, samples heated to about 90° C. to about 105° C. typically contain a combination of Form B and amorphous cilostazol at varying percentages of each. However, some Form C and, potentially, Form A, may be crystallized using these heating temperatures when the heating rate is held constant as taught herein and, at a hold time of about zero minutes. As heating temperature is increased above 105° C., the purity of Form B is increased. For example, a temperature of about 120° C., hold time of about zero minutes, and heating rate of about 10° C./minute provides pure Form B (within detectable limits). Temperatures above about 130° C. will initiate melting of the resulting Form B polymorph.

Alternately, when maintaining a constant heating rate of about 10° C./minute, lower temperatures can be employed using longer hold times. For example, with temperatures below about 105° C., hold times of about 5 minutes and greater will provide purities of Form B similar to purities obtained with heating temperatures greater than about 105° C. with hold times of about zero minutes. Depending upon the heating variables used, more particularly, holding the heating rate constant, with a heating temperature of about 100° C., a hold time of about 5 minutes essentially eliminates amorphous cilostazol. Under these conditions the resulting product is predominately Form B, with the remaining portion being predominately Form C.

Moreover, pure Form B can also be formed by using heating temperatures greater than about 100° C. and, for small samples increased hold times. For examples when maintaining a constant heating rate of about 110° C. per minute, a heating temperature of about 110° C. and hold time of about 5 minutes also provides pure Form B. Other variations of the heating variables will also provide pure Form B providing the heating temperature does not exceed the melting point of Form B and the temperature is held for a time period sufficient to complete the formation of pure Form B of the present invention. As such, the scope of the present invention is not limited to these exemplifications.

After the heating step is completed and the desired polymorphic form(s) are obtained, the resulting cilostazol is recooled. With regard to Form B, the cilostazol is actively recooled or allowed to passively recool, preferably at a controlled rate (preferably about 10° C./minute), to about ambient temperature.

Preferably, Form B is produced in a pure form (devoid of detectable amounts of other polymorphic forms of cilostazol as determined by FTIR, FT-Raman and/or X-Ray powder diffraction, as appropriate), or in substantially pure form having negligible other amounts of detectable polymorphic forms of cilostazol.

For the preparation of pure Form C of the present invention, the heating step for the preparation of Form B as described herein is used providing at least some Form C (as detected using DSC) is present in the sample. It is preferred to use a sample that has a higher rather than lower percentage of Form C. For example, the heating step for the preparation of Form B above wherein the heating rate is held constant, a heating temperature of about 100° C., and hold time of about 5 minutes provides a good starting material for the preparation of pure Form C.

Following such heating step, the sample is actively recooled, preferably in a controlled manner, to about ambient temperature or below. Preferred cooling temperatures are from about ambient temperature to about −80° C., and more preferred from about −10° C. to about 10° C.

For the preparation of purer forms of Form C and, particularly, pure Form C, the recooled sample containing at least some Form C is reheated to a temperature which is greater than about the melting point of Form B (about 135° C. to about 137° C.) but below the melting point of Form C (about 147° C. to about 149° C.). The temperature typically is held for a period of time that is sufficiently long to ensure the complete melt of Form B. Providing all Form B present is melted during this reheating step, pure Form C is formed during the final re-cooling step from the melted Form B, using the remaining, un-melted Form C as seed crystals for the resulting pure Form C. If the Form B crystals are not completely melted during the re-heating step, this resulting material will predominately comprise Form C with the unmelted portion of Form B remaining as Form B. As with all of the processes set forth herein, it is referred to maintain the rate of heating constant at about 10° C./minute.

During the final recooling step, the cilostazol is actively recooled or allowed to passively recool, preferably at a controlled rate, to about ambient temperature. preferably, Form C is produced in a pure form (devoid of detectable amounts of other polymorphic forms of cilostazol as determined by FTIR, FT-Raman, and/or X-ray powder diffraction, as appropriate), or in substantially pure form having negligible amounts of other detectable polymorphic forms of cilostazol.

The present invention also provides pharmaceutical formulations comprising pure Form B, pure Form C, or pure amorphous cilostazol, either as the sole active ingredient or in combination with other active ingredients including, for example, other polymorphic forms of cilostazol or other pharmaceutically active agents, at least one pharmaceutically acceptable carrier, diluent, and/or excipient. Combinations of more than one polymorphic form of cilostazol are prepared via the described crystallization procedures or, for more precise combinations, via blending of pure or known polymorphic ratios. Preferred polymorphic combinations include, for example, Form B with Form C, Form A, and/or amorphous cilostazol; Form C with Form B, Form A, and/or amorphous cilostazol, and amorphous cilostazol with Form B, Form C and/or Form A of cilostazol.

Preferably, the novel crystalline forms of cilostazol, Form B and Form C, and amorphous cilostazol, are in pure form. Pure form includes those samples of either Form B, Form C, or amorphous cilostazol, individually, that do not possess detectable amounts of any additional form of cilostazol as evidenced by XRD, FTIR, and/or FT-Raman analysis.

For the most effective administration of the polymorphic forms of the present invention, it is preferred to prepare a pharmaceutical formulation preferably in unit dose form, comprising one or more of the active ingredients of the present invention and one or more pharmaceutically acceptable carrier, diluent, or excipient.

As used herein, the term "active ingredient" refers to any of the embodiments set forth herein, particularly Form B, Form C, and amorphous cilostazol, individually and in combination among polymorphic forms of the present invention or other cilostazol polymorphic forms. More preferably polymorphic Form B and Form C of the present invention are used in pure form in the pharmaceutical formulations of the present invention.

Preferred pharmaceutical formulations may include, without being limited by the teachings as set forth herein, a solid dosage form, of Form B, Form C and/or amorphous cilostazol, of the present invention in combination with at least one pharmaceutically acceptable excipient, diluted by an excipient or enclosed within such a carrier that can be in the form of a capsule, sachet, tablet, buccal, lozenge, paper, or other container. Additionally, such pharmaceutical formulation may include a liquid formulation prepared from Form B, Form C and/or amorphous cilostazol API of the present invention in combination with at least one pharmaceutically acceptable excipient, diluted by an excipient or enclosed within an appropriate carrier. When the excipient serves as a diluent, it may be a solid, semi-solid, or liquid material which acts as a vehicle, carrier, or medium for the active ingredient(s). Thus, the formulations can be in the form of tablets, pills, powders, elixirs, suspensions, emulsions, solutions, syrups, capsules (such as, for example, soft and hard gelatin capsules), suppositories, sterile injectable solutions, and sterile packaged powders.

Examples of suitable excipients include, but are not limited to, starches, gum arabic, calcium silicate, microcrystalline cellulose, polyvinylpyrrolidone, cellulose, water, syrup, and methyl cellulose. The formulations can additionally include lubricating agents such as, for example, talc, magnesium stearate and mineral oil; wetting agents; emulsifying and suspending agents; preserving agents such as methyl- and propyl-hydroxybenzoates; sweetening agents; or flavoring agents. Polyols, buffers, and inert fillers may also be used. Examples of polyols include, but are not limited to: mannitol, sorbitol, xylitol, sucrose, maltose, glucose, lactose, dextrose, and the like. Suitable buffers encompass, but are not limited to, phosphate, citrate, tartrate, succinate, and the like. Other inert fillers which may be used encompass those which are known in the art and are useful in the manufacture of various dosage forms. If desired, the solid pharmaceutical compositions may include other components such as bulking agents and/or granulating agents, and the like. The compositions of the invention can be formulated so as to provide quick, sustained, controlled, or delayed release of the active ingredient after administration to the patient by employing procedures well known in the art.

In certain embodiments of the present invention, the active ingredient(s) may be made into the form of dosage units for oral administration. The active ingredient(s) may be mixed with a solid, pulverant carrier such as, for example, lactose, saccharose, sorbitol, mannitol, starch, amylopectin, cellulose derivatives or gelatin, as well as with an antifriction agent such as for example, magnesium stearate, calcium stearate, and polyethylene glycol waxes. The mixture is then pressed into tablets or filled into capsules. If coated tablets, capsules, or pulvules are desired, such tablets, capsules, or pulvules may be coated with a concentrated solution of sugar, which may contain gum arabic, gelatin, talc, titanium dioxide, or with a lacquer dissolved in the volatile organic solvent or mixture of solvents. To this coating, various dyes may be added in order to distinguish among tablets with different active compounds or with different amounts of the active compound present.

Soft gelatin capsules may be prepared in which capsules contain a mixture of the active ingredient(s) and vegetable oil or non-aqueous, water miscible materials such as, for example, polyethylene glycol and the like. Hard gelatin capsules may contain granules or powder of the active ingredient in combination with a solid, pulverulent carrier, such as, for example, lactose, saccharose, sorbitol, mannitol, potato starch, corn starch, amylopectin, cellulose derivatives, or gelatin.

Tablets for oral use are typically prepared in the following manner, although other techniques may be employed. The solid substances are gently ground or sieved to a desired particle size, and a binding agent is homogenized and suspended in a suitable solvent. The active ingredient(s) and auxiliary agents are mixed with the binding agent solution. The resulting mixture is moistened to form a uniform suspension. The moistening typically causes the particles to aggregate slightly, and the resulting mass is gently pressed through a stainless steel sieve having a desired size. The layers of the mixture are then dried in controlled drying units for a pre-determined length of time to achieve a desired particle size and consistency. The granules of the dried mixture are gently sieved to remove any powder. To this mixture, disintegrating, anti-friction, and anti-adhesive agents are added. Finally, the mixture is pressed into tablets using a machine with the appropriate punches and dies to obtain the desired tablet size.

Liquid preparations for oral administration are prepared in the form of solutions, syrups, or suspensions with the latter two forms containing, for example, active ingredient(s), sugar, and a mixture of ethanol, water, glycerol, and propylene glycol. If desired, such liquid preparations contain coloring agents, flavoring agents, and saccharin. Thickening agents such as carboxymethylcellulose may also be used.

As such, the pharmaceutical formulations of the present invention are preferably prepared in a unit dosage form, each dosage unit containing from about 10 mg to about 300 mg, preferably from about 25 mg to about 125 mg and more preferably from about 40 mg to about 110 mg of the cilostazol active ingredient(s). Other pharmaceutically active agents can also be added to the pharmaceutical formulations of the present invention at therapeutically effective dosages. In liquid form, unit doses contain from about 10 to about 300 mg, preferably about 25 mg to about 125 mg and more preferably about 40 mg to about 110 mg of such cilostazol active ingredient(s).

The term "unit dosage form" refers to physically discrete units suitable as unitary dosages for human subjects/patients or other mammals, each unit containing a predetermined quantity of active ingredient calculated to produce the desired therapeutic effect, in association with preferably, at least one pharmaceutically acceptable carrier, diluent, or excipient.

The invention also provides methods of treating a subject (e.g., mammal, particularly humans) comprising administering to a subject in need of such treatment a therapeutically effective amount of at least one active ingredient, formulation thereof, or unit dose forms thereof, each as described herein. The active ingredient(s) are used to inhibit cellular phosphodiesterase, particularly phosphodiesterase III. The primary use for such active ingredient(s) is for the reduction of intermittent claudication in such subjects, typically manifested by an increased walking distance. The cilostazol active ingredients of the present invention may also be used for the treatment of other disease states related to vasodilation including, for example, stroke and antiplatelet effects. Such active ingredients may also increase plasma high density lipoprotein cholesterol and apolipoprotein in subjects in need of such treatment as well as being used to treat sexual dysfunction.

As used herein, the term "treatment", or a derivative thereof, contemplates partial or complete inhibition of the stated disease state such as, for example, intermittent claudication, when an active ingredient of the present invention is administered prophylactically or following the onset of the disease state for which such active ingredient of the present invention is administered. For the purposes of the present invention, "prophylaxis" refers to administration of the active ingredient(s) to a subject to protect the subject from any of the disorders set forth herein, as well as others.

The typical active daily dose of the cilostazol active ingredient(s) will depend on various factors such as, for example, the individual requirement of each patient, the route of administration, and the disease state. An attending physician may adjust the dosage rate based on these and other criteria if he or she so desires. A suitable daily dosage, typically administered b.i.d. in equally divided doses, is from about 50 mg to about 250 mg, preferably from about 80 mg to about 240 mg, and more preferably from about 100 mg to about 200 mg. A preferred range is from about 100 mg to about 200 mg total daily dose. It should be appreciated that daily doses other than those described above may be administered to a subject, as appreciated by an attending physician.

The following examples are for illustrative purposes only and are not intended to limit the scope of the claimed invention.

EXAMPLE 1

Preparation of Pure Form B of Cilostazol

A sample of approximately 5 mg of Form A of cilostazol was placed in a vented, sealed aluminum holder and placed in a DSC furnace. Under a nitrogen purge of 40 milliliters per minute, the sample was heated from a temperature of 30° C. to approximately 200° C. (past the melting point of Form A) at a heating rate of 10° C. per minute. The molten cilostazol was cooled within the furnace to approximately 0° C. at a cooling rate of approximately 10° C. per minute. The cooled cilostazol was reheated from 0° C. to 110° C., and held at 110° C. for five minutes. After holding the cilostazol at 110° C. for five minutes, the cilostazol was cooled to 0° C. at a rate of 10° C. per minute. The cilostazol was then reheated in an undisturbed state by DSC at a rate of 10° C. per minute to a final temperature about 170° C., the sample showed an endothermic peak for Form B of cilostazol at approximately 138° C. (onset observed at about 136° C.) with a minor peak at 149° C. which relates to Form C (onset observed at about 147° C.).

EXAMPLE 1A

Preparation of Pure Form B of Cilostazol

A sample of approximately 20 mg of Form A of cilostazol was placed in a vented, sealed aluminum holder and placed in a DSC furnace. Under a nitrogen purge of 40 milliliters per minute, the sample was heated from a temperature of 30° C. to approximately 200° C. (past the melting point of Form A) at a heating rate of 10° C. per minute. The molten cilostazol was cooled within the furnace to approximately 0° C. at a cooling rate of approximately 10° C. per minute. The cooled cilostazol was reheated from 0° C. to 110° C., and held at 110° C. for five minutes. After holding the cilostazol at 110° C. for five minutes, the cilostazol was cooled to 30° C. at a rate of 10° C. per minute. The sample was removed and analyzed by XRD, FTIR and FT-Raman which confirmed the sample as 100% Form B of cilostazol.

EXAMPLE 1B

Transformation of Pure Form B of Cilostazol to Form A of Cilostazol

The resultant sample of Example 1A was disturbed with scratching, which caused the cilostazol sample to undergo a solid state phase transformation at approximately 119° C. followed by an endotherm of melt at approximately 160° C. (Form A) during heating by DSC from 30° C. to approximately 200° C. at 10° C. per minute.

EXAMPLE 2

Preparation of Pure/Essentially Pure Form C of cilostazol

A sample of approximately 14 mg of Form A of cilostazol was placed in a vented, sealed aluminum holder and placed in a DSC furnace. Under a nitrogen purge of 40 milliliters per minute, the sample was heated from a temperature of 30° C. to approximately 200° C. (past the melting point of Form A) at a heating rate of 10° C. per minute. The molten cilostazol was cooled to approximately 0° C. at a cooling rate of approximately 10° C. per minute. The cooled cilostazol was reheated from 0° C. to 0° C., and held at 10° C. for five minutes. After holding the cilostazol at 100° C. for five minutes, the cilostazol was cooled to 0° C. at a rate of 10° C. per minute. The cilostazol was then reheated at a rate of 1 0° C. per minute to a temperature of 45° C. and held at 145° C. for 5 minutes, after which time the cilostazol was then recooled to 0° C. at a rate of 10° C. per minute. Upon reheating in an undisturbed state, by DSC, the sample showed single endothermic peak for Form C at about 149° C. (onset of about 146° C.).

EXAMPLE 2A

Preparation of Pure Form C of Cilostazol

A sample of approximately 22 mg of Form A cilostazol was placed in a vented, sealed aluminum holder and placed in a DSC furnace under a nitrogen purge of 40 milliliters per minute, the sample was reheated from a temperature of 30° C. to approximately 200° C. (past the melting point of Form A) at a heating rate of 10° C. per minute. The molten cilostazol was cooled to approximately 0° C. at a cooling rate of approximately 10° C. per minute. The cooled cilostazol was reheated from 0° C. to 100° C., and held at 100° C. for five minutes. After holding the cilostazol at 100° C. for five minutes, the cilostazol was cooled to 0° C. at a rate of 10° C. per minute. The cilostazol was then reheated at a rate of 0° C. per minute to a temperature of 145° C. and held for five minutes, after which time the cilostazol was then recooled to 30° C. at a rate of 10° C. per minute. A single crystal was obtained from the DSC pan and analyzed by this technique. The structure was found to have a different polymorphic form than that of Form A or Form B (identified in Example 1). The cilostazol sample displayed a unique XRD powder pattern, FTIR and FT-Raman spectra and was identified as 100% Form C of cilostazol.

EXAMPLE 2B

Transformation from Form C to Form A of Cilostazol

When the sample is stressed and reheated (as detailed in Example 2A), the sample undergoes a solid state phase transformation at approximately 147° C. followed by an endotherm of melt at about 160° C. (Form A) during heating by DSC from 30° C. to approximately 200° C. at 10° C. per minute. This disturbance of sample is believed to induce nucleation which preferentially causes Form A of cilostazol to form upon heating.

EXAMPLE 3

Preparation of a Combination of Form B of Cilostazol and Form A of Cilostazol (about 60:40)

A sample of approximately 7 mg of Form A cilostazol was placed in a vented, sealed aluminum holder and placed in a DSC furnace under a nitrogen purge of 40 milliliters per minute, the sample was heated from a temperature of 30° C. to approximately 200° C. (past the melting point of Form A) at a heating rate of 10° C. per minute. The molten cilostazol was cooled to approximately 0° C. at a cooling rate of approximately 10° C. per minute. The cooled cilostazol was reheated from 0° C. to 130° C. The cilostazol was then cooled to 0° C. at a rate of 10° C. per minute.

The cilostazol was then reheated in an undisturbed state by DSC from 0° C. to 200° C. at 10° C. per minute. Two endotherms of melt were observed at approximately 138° C. (Form B) and 161° C. (Form A) in a heat of enthalpy ratio of approximately 60:40, respectively, with the relative amount of Form B and Form A further variable on the heat of enthalpy of each polymorphic form.

EXAMPLE 4

Preparation of a combination of Form B of cilostazol and Form A of cilostazol (about 60:40)

A sample of approximately 6 mg of Form A cilostazol was placed in a vented, sealed aluminum holder and placed in a DSC furnace under a nitrogen purge of 40 milliliters per minute, the sample was heated from a temperature of 30° C. to approximately 200° C. (past the melting point of Form A) at a heating rate of 0° C. per minute. The molten cilostazol was cooled to approximately 0° C. at a cooling rate of approximately 10° C. per minute. The cooled cilostazol was reheated from 0° C. to 120° and held for five minutes. After holding for five minutes, the cilostazol was cooled to 0° C. at a rate of 10° C. per minute.

The cilostazol was reheated in an undisturbed state by DSC from 0° C. to 200° C. at 0° C. per minute. Two endotherms of melt were observed at approximately 138° C. (Form B) (onset at about 135° C. ) and 161° C. (Form A) (onset at about 159° C) in a heat of enthalpy ratio of approximately 60:40, respectively, with the relative amount of Form B and Form A further variable on the heat of enthalpy of each polymorphic form.

EXAMPLE 5

Preparation of a Combination of Form A of Cilostazol, Form B of Cilostazol and Form C of Cilostazol A sample of approximately 5 mg of Form A cilostazol was placed in a vented, sealed aluminum holder and placed in a DSC furnace under a nitrogen purge of 40 milliliters per minute, the sample was heated from a temperature of 30° C. to approximately 200° C. (past the melting point of Form A) at a heating rate of 10° C. per minute. The molten cilostazol was cooled to approximately 0° C. at a cooling rate of approximately 10° C. per minute. The cooled cilostazol was reheated from 0° C. to 110° C., and held at 110° C. for 30 minutes. After holding the sample for 30 minutes at 110° C., the cilostazol was cooled to 0° C. at a rate of 10° C. per minute.

The cilostazol was reheated in an undisturbed state by DSC from 0° C. to 200° C. at 10° C. per minute. Three endotherms of melt were observed at approximately 138° C. (onset at about 136° C.) (Formn B), 149° C. (onset at about 147° C.) (Form C) and 161° C. (onset at about 159° C.) (Form A) in a heat of enthalpy ratio of approximately 80:20:10, respectively, with the relative amount of Form B, Form C and Form A further variable on the heat of enthalpy of each polymorphic form.

EXAMPLE 6

Preparation of Form B: Form C (about 90:10)

A sample of approximately 7 mg of Form A of cilostazol was placed in a vented, sealed aluminum holder and placed in a DSC furnace. Under a nitrogen purge of 40 milliliters per minute, the sample was heated from a temperature of 30° C. to a temperature of approximately 200° C. (past the melting point of Form A) at a heating rate of 10° C. per minute. The molten cilostazol was cooled within the furnace to approximately 0° C. at a cooling rate of approximately 10° C. per minute. The cooled cilostazol was reheated from 0° C. to 130° C., and held at 130° C. for five minutes. After holding the cilostazol at 130° C. for the five minutes, the cilostazol was cooled to 0° C. at a rate of 10° C. per minute. The cilostazol was then reheated in an undisturbed state by DSC at a rate of 10° C. per minute to a final temperature above 170° C. The sample showed an endothermic peak for Form B of cilostazol at approximately 138° C. (onset at about 135° C.) with a minor peak at 149° C. (onset at about 147° C.) which relates to Form C. The peaks show a Form B to Form C peak area ratio of approximately 90:10, respectively, with the relative amount of Form B to Form C further variable on the heat of enthalpy of each polymorphic form.

EXAMPLE 7

Preparation of pure Form B of Cilostazol

A sample of approximately 8 mg of Form A of cilostazol was placed in a vented, sealed aluminum holder and placed in a DSC furnace. Under a nitrogen purge of 40 milliliters per minute, the sample was heated from a temperature of 30° C. to approximately 200° C. (past the melting point of Form A) at a heating rate of 10° C. per minute. The molten cilostazol was cooled within the furnace to approximately 0° C. at a cooling rate of approximately 10° C. per minute. The cooled cilostazol was reheated from 0° C. to 120° C. The cilostazol was cooled to 0° C. at a rate of 10° C. per minute. The cilostazol was then reheated in an undisturbed state by DSC at a rate of 0° C. per minute to a final temperature above 170° C. The sample showed an endothermic peak for Form B of cilostazol at approximately 139° C. (onset at about 136° C.) with a minor peak at 147° C. (onset at about 149° C.) which relates to Form C.

EXAMPLE 8

Preparation of Form B: Form C Cilostazol (about 66:34)

A sample of approximately 8 mg of Form A of cilostazol was placed in a vented, sealed aluminum holder and placed in a DSC furnace. Under a nitrogen purge of 40 milliliters per minute, the sample was heated from a temperature of 30° C. to approximately 200° C. (past the melting point of Form A) at a heating rate of 10° C. per minute. The molten cilostazol was cooled within the furnace to approximately 0° C. at a cooling rate of approximately 10° C. per minute. The cooled cilostazol was reheated from 0° C. to 110° C. The cilostazol was then cooled to 0° C. at a rate of 10° C. per minute. The cilostazol was then reheated in an undisturbed state by DSC at a rate of 10° C. per minute to a final temperature above 170° C. The sample showed an endothermic peak for Form B of cilostazol at approximately 138° C. (onset at about 135°) with a minor peak at 149° C. (onset at about 147° C.) which relates to Form C. The peaks show a Form B to Form C peak area ratio of approximately 66:34, respectively, with the relative amount of Form B to Form C further variable on the heat of enthalpy of each polymorphic form.

EXAMPLE 9

Preparation of Form B: Form C Cilostazol (about 92:8)

A sample of approximately 7 mg of Form A of cilostazol was placed in a vented, sealed aluminum holder and placed in a DSC furnace. Under a nitrogen purge of 40 milliliters per minute, the sample was heated from a temperature of 30° C. to a temperature of approximately 200° C. (past the melting point of Form A) at a heating rate of 10° C. per minute. The molten cilostazol was cooled within the furnace to approximately 0° C. at a cooling rate of approximately 0° C. per minute. The cooled cilostazol again was heated from 0° C. to 130° C., and held at 30° C. for 30 minutes. After holding the cilostazol at 130° C. for 30 minutes, the cilostazol was cooled to 0° C. at a rate of 0° C. per minute. The cilostazol was then reheated in an undisturbed state by DSC at a rate of 10° C. per minute to a final temperature above 170° C. The sample showed an endothermic peak for Form B of cilostazol at approximately 199° C. (with a minor peak at 149° C. which relates to Form C. The peaks show a Form B to Form C peak area ratio of approximately 92:8, respectively, with the relative amount of Form B to Form C further variable on the heat of enthalpy of each polymorphic form.

EXAMPLE 10

Preparation of Form B: Form C Cilostazol (about 87:13)

A sample of approximately 5 mg of Form A of cilostazol was placed in a vented, sealed aluminum holder and placed in a DSC furnace. Under a nitrogen purge of 40 milliliters per minute, the sample was heated from a temperature of 30° C. to approximately 200° C. (past the melting point of Form A) at a heating rate of 10° C. per minute. The molten cilostazol was cooled within the furnace to approximately 0° C. at a cooling rate of approximately 10° C. per minute. The cooled cilostazol was reheated from 0° C. to 100° C., and held at 100° C. for five minutes. After holding the cilostazol for the five minutes, the cilostazol was cooled to 0° C. at a rate of 10° C. per minute. The cilostazol was then reheated in an undisturbed state by DSC at a rate of 10° C. per minute to a final temperature above 170° C. The sample showed an endothermic peak for Form B of cilostazol at approximately 138° C. (onset at about 135° C.) with a minor peak at 149° C. (onset at about 147° C. which relates to Form C. The peaks show a Form B to Form C peak area ratio of approximately 87:13, respectively, with the relative amount of Form B to Form C further variable on the heat of enthalpy of each polymorphic form.

EXAMPLE 11

Preparation of Form B: Form C Cilostazol (about 83:17)

A sample of approximately 6 mg of Form A of cilostazol was placed in a vented, sealed aluminum holder and placed in a DSC furnace. Under a nitrogen purge of 40 milliliters per minute, the sample was heated from a temperature of 30° C. to approximately 200° C. (past the melting point of Form A) at a heating rate of 10° C. per minute. The molten cilostazol was cooled within the furnace to approximately 0° C. at a cooling rate of approximately 10° C. per minute. The cooled cilostazol was reheated from 0° C. to 120° C., and held at 120° C. for 30 minutes. After holding the cilostazol at 120° C. for 30 minutes, the cilostazol was cooled to 0° C. at a rate of 10° C. per minute. The cilostazol was then reheated in an undisturbed state by DSC at a rate of 10° C. per minute to a final temperature above 170° C. The sample showed an endothermnic peak for Form B of cilostazol at approximately 139° C. (onset at about 136° C.) with a minor peak at 149° C. (onset at about 147° C. which relates to Form C. The peaks show a Form B to Form C peak area ratio of approximately 83:17, respectively, with the relative amount of Form B to Form C further variable on the heat of enthalpy of each polymorphic form.

EXAMPLE 12

Hot Stage Microscopy

A sample of Form A of cilostazol was placed on a glass slide and inserted into a hot stage microscope furnace. Hot stage microscopy provides an analytical technique that allows for heat manipulation of the cilostazol sample while visual observing changes utilizing a microscope apparatus. Samples of Form A cilostazol were heated to approximately 170° C. and held until visually melted, then cooled by removing the glass slide and placing it on a laboratory bench or other suitable place to cool in an area free of potential contamination. The sample was then heated under various conditions involving varying heating rate (HR), maximum temperature (70° C., 80° C., 90° C. and 100° C.) and hold times (T), XRD was performed on each sample to monitor the degree of crystallinity as well as crystalline forms present.

At 70° C.: a heating rate 1 degree per minute held for 5 minutes resulted in amorphous cilostazol; amorphous with about 5% Form B (HR=2, T=5); amorphous (HR=5, T=5); amorphous with about 5% Form B (HR=2, T=5); amorphous with about 20% Form B (HR =2, T =15); amorphous with about 60% Form B (HR=2, T=30); and trace amount of amorphous with about 95% Form B (HR=2, T=45).

At 80° C.: about 100% Form B (HR=1, T=5); about 80% Form B with about 20% Form A (HR=2, T=5); about 100% Form B with trace amorphous (HR=5, T=15); about 40% Form B with about 60% Form A (HR=2, T=2); about 20% Form B with about 80% Form A (HR=2, T=15); about 5% Form B with about 95% Form A (HR=2, T=30); and about 100% Form A (HR=2, T=45).

At 90° C.: about 100% Form A (HR=1, T=5); about 95% Form B and trace of Form A (HR=2, T=5); about 80% Form B (HR=5, T=5); about 95% Form B and trace Form A (HR=2, T=5); about 100% Form A (HR=2, T=15); about 100% Form A (HR=2, T=30); and about 100% Form A (HR =2 T=45).

At 100° C.: Form A with trace of Form B (HR=1, T=5); about 100% Form A (HR=2, T=25); and about 50% Form A and about 50% Form B (HR=5, T=5).

Hot stage microscopy was performed to provide an indication of the trends of the solid state transformations of the cilostazol. If an alternative sample holder is used instead of glass (e.g., aluminum) the cooling process will need to be altered to avoid stress to the amorphous sample which will create nucleation sites that cause Form A to preferentially form upon reheating.

| Formulation 1 Hard gelatin 50 mg capsules are prepared using the following ingredients: | |
|---|---|
| | Quantity (mg/capsule) |
| active ingredient(s) ethanedioate | 50 |
| starch, dried | 200 |
| magnesium stearate | 10 |
| Total | 260 |

The above ingredients are mixed and filled into hard gelatin Capsules in 260 mg quantities.

| Formulation 2 A 100 mg tablet is prepared using the ingredients below: | |
|---|---|
| | Quantity (mg/tablet) |
| active ingredient(s) | 100 |
| cellulose, microcrystalline | 400 |
| silicon dioxide, fumed | 10 |
| stearic acid | 5 |
| Total | 515 |

The components are blended and compressed to form tablets each weighing 515 mg.

| Formulation 3 Tablets each containing 50 mg of active ingredient are made as follows: | |
|---|---|
| active ingredient | 50 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 140 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No.60 mesh U.S. sieve, are then added to the granules which, after mixing, are compressed on a tablet machine to yield tablets each weighing 140 mg.

| Formulation 4 Capsules each containing 50 mg of medicament are made as follows: | |
|---|---|
| active ingredient | 50 mg |
| starch | 59 mg |
| microcrystalline cellulose | 59 mg |
| magnesium stearate | 2 mg |
| Total | 170 mg |

The active ingredient, cellulose, starch and magnesium stearate are blended, passed through a No. 45 mesh U.S. sieve, and filled into hard gelatin capsules in 170 mg quantities.

The examples and embodiments as set forth in the detailed description are for illustrative purposes only and do not limit the scope of the invention.

What is claimed is:

1. A process for preparing Form C of cilostazol, comprising the steps of:
    melting a cilostazol starting material;
    cooling the melted cilostazol; and,
    heating the cooled cilostazol sufficient to induce a cold crystallization of Form C of cilostazol.

2. The process of claim 1, wherein the heating step is accomplished by:

elevating the temperature of the cooled cilostazol to a temperature range from above the cold crystallization temperature to at less than about 130° C.; and, holding said temperature for a period of time sufficient to induce the crystallization of said Form C.

3. The process of claim 1, wherein the step of cooling the melted cilostazol comprises cooling to a temperature at or below about the glass transition temperature.

4. The process of claim 2, wherein the step of cooling the melted cilostazol comprises cooling to a temperature at or below about the glass transition temperature.

5. The process of claim 1, further comprising the step of: recooling the heated cilostazol.

6. A process for further purifying Form C of cilostazol, comprising the process of claim 5 and further comprising the step of reheating the recooled cilostazol to a temperature of from about 138° C. to about 147° C.

7. The process of claim 6, further comprising the step of: re-recooling the reheated cilostazol.

8. Form C of cilostazol prepared by the process of claim 1.

9. Form C of cilostazol prepared by the process of claim 2.

10. Form C of cilostazol prepared by the process of claim 3.

11. Form C of cilostazol prepared by the process of claim 4.

12. Form C of cilostazol prepared by the process of claim 5.

13. Form C of cilostazol prepared by the process of claim 6.

14. Form C of cilostazol prepared by the process of claim 7.

* * * * *